US011071778B2

(12) United States Patent
Manting et al.

(10) Patent No.: US 11,071,778 B2
(45) **Date of Patent: *Jul. 27, 2021**

(54) COMBINATION PRODUCT FOR USE IN TUMOR VACCINATION

(71) Applicant: DCPRIME B.V., Leiden (NL)

(72) Inventors: Erik Hans Manting, Leiden (NL); Satwinder Kaur Singh, Leiden (NL); Adriana Maria Kruisbeek, Leiden (NL); Vinod Sommandas, Leiden (NL)

(73) Assignee: DCPRIME B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/858,326

(22) Filed: Apr. 24, 2020

(65) Prior Publication Data

US 2020/0397883 A1 Dec. 24, 2020

Related U.S. Application Data

(63) Continuation of application No. PCT/NL2019/050451, filed on Jul. 16, 2019.

(30) Foreign Application Priority Data

Jul. 16, 2018 (EP) .................................... 18183694
Apr. 25, 2019 (EP) .................................... 19170999

(51) Int. Cl.

| | |
|---|---|
| ***A61K 39/05*** | (2006.01) |
| ***A61P 35/00*** | (2006.01) |
| ***A61K 39/00*** | (2006.01) |
| ***A61K 39/08*** | (2006.01) |
| ***A61K 9/00*** | (2006.01) |
| ***A61K 35/15*** | (2015.01) |

(52) U.S. Cl.

CPC ............ *A61K 39/08* (2013.01); *A61K 9/0019* (2013.01); *A61K 35/15* (2013.01); *A61P 35/00* (2018.01); *A61K 2039/54* (2013.01); *A61K 2039/545* (2013.01); *A61K 2039/585* (2013.01)

(58) Field of Classification Search

None

See application file for complete search history.

(56) References Cited

U.S. PATENT DOCUMENTS

| | | | |
|---|---|---|---|
| 5,876,989 | A | 3/1999 | Berg et al. |
| 6,680,301 | B2 | 1/2004 | Berg et al. |
| 7,700,546 | B2 | 4/2010 | Mekada et al. |
| 8,507,443 | B2 | 8/2013 | Mekada et al. |
| 2004/0057935 | A1 | 3/2004 | Yu et al. |
| 2013/0330399 | A1 | 12/2013 | Reisfeld et al. |

FOREIGN PATENT DOCUMENTS

| | | | |
|---|---|---|---|
| EP | 1894575 B1 | 2/2013 | |
| EP | 2931878 B1 | 11/2016 | |
| WO | WO 1996/007432 | A1 | 3/1996 |
| WO | WO 1996/040200 | A1 | 12/1996 |
| WO | WO 2000/054802 | A2 | 9/2000 |
| WO | WO 2001/049317 | A2 | 7/2001 |
| WO | WO 2002/023994 | A1 | 3/2002 |
| WO | WO 2002/044395 | A1 | 6/2002 |
| WO | WO 2002/044396 | A1 | 6/2002 |
| WO | WO 2002/080648 | A2 | 10/2002 |
| WO | WO 2003/020309 | A2 | 3/2003 |
| WO | WO 2009/019320 | A2 | 2/2009 |
| WO | WO 2009/034172 | A1 | 3/2009 |
| WO | WO 2009/127988 | A1 | 10/2009 |
| WO | WO 2011/018636 | A2 | 2/2011 |
| WO | WO 2012/136824 | A1 | 10/2012 |
| WO | WO 2014/006058 | A1 | 1/2014 |
| WO | WO 2014/138314 | A1 | 9/2014 |
| WO | WO 2015/073801 | A1 | 5/2015 |
| WO | WO 2018/017020 | A1 | 1/2018 |
| WO | WO 2020/017962 | A1 | 1/2020 |

OTHER PUBLICATIONS

International Search Report and Written Opinion for PCT International Application No. PCT/NL2019/050451, dated Oct. 4, 2019, 13 pages.

Alemany, "Oncolytic Adenoviruses in Cancer Treatment", Biomedicines, 2014, 2(1): 36-49.

Alibakhshi et al., "Targeted cancer therapy through antibody fragments-decorated nanomedicines", J Control Release, 2017, 268: 323-334.

Andtbacka et al., "Talimogene Laherparepvec Improves Durable Response Rate in Patients With Advanced Melanoma", Journal of Clinical Oncology, 2015, 22(25): 2780-2788.

Anguille et al., "Dendritic cell vaccination as postremission treatment to prevent or delay relapse in acute myeloid leukemia", Blood, Oct. 2017, 130(15): 1713-1721.

Awate et al., "Mechanisms of Action of Adjuvants" Frontiers in Immunology, 2013, 4(114): 1-10.

Bell et al., "Crystal structure of nucleotide-free diphtheria toxin", Biochemistry, 1997, 36(3): 481-488.

(Continued)

*Primary Examiner* — Padmavathi Baskar

(74) *Attorney, Agent, or Firm* — Lathrop GPM LLP; James H. Velema; Judith L. Stone-Hulslander

(57) ABSTRACT

The present invention relates to a combination product for use in eliciting an immune response against a tumor in a subject, said product comprising: —an immunogenic composition comprising a non-human antigenic polypeptide as an immunogen, or comprising a nucleic acid encoding said immunogen, and optionally one or more pharmaceutically-acceptable carriers, adjuvants, excipients and/or diluents; and—said non-human antigenic polypeptide, or a nucleic acid encoding said polypeptide; wherein said polypeptide or said nucleic acid is prepared for intratumoral delivery. The invention also provides fusion proteins and protein-protein conjugates that can be used in the medical methods described herein.

20 Claims, 6 Drawing Sheets

Figure 1A:
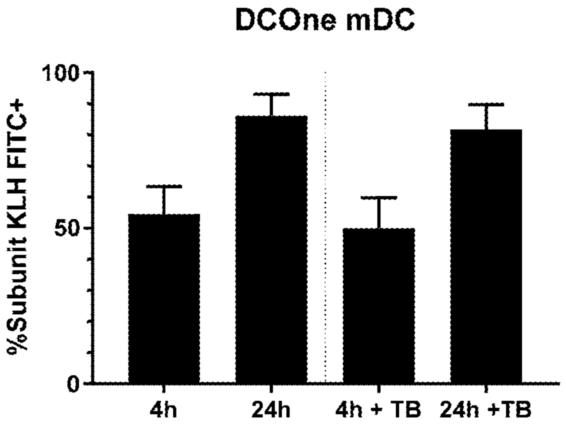

Specification includes a Sequence Listing.

(56) References Cited

OTHER PUBLICATIONS

Bender et al., "Inactivated influenza virus, when presented on dendritic cells, elicits human CD8+cytolytic T cell responses", J. Exp. Med, 1995, 182: 1663-1671.
Bennett et al., "Help for cytotoxic-T-cell responses is mediated by CD40 signaling", *Nature*, 1998, 393: 478-480.
Bergmann et al., "An endogenously synthesized decamer peptide efficiently primes cytotoxic T cells specific for the HIV-1 envelope glycoprotein", *Eur J Immunol.*, 1993, 23(11): 2777-2781.
Bommareddy et al., "Integrating oncolytic viruses in combination cancer immunotherapy", Nature Reviews Immunology, 2018, 18: 498-513.
Buzzi et al., "Cancer immunity after treatment of Ehrlich tumor with diphtheria toxin", Cancer Res., Dec. 1974, 34(12): 3481-3486.
Buzzi et al., "CRM197: Effects of intravenous administration to advanced cancer patients", Cancer Res., Apr. 2004, 64(7 Supplement): 878.
Buzzi et al., "Diphtheria toxin in cancer therapy", The Lancet, 1974, 1(7858): 628-629.
Buzzi, "Diphtheria toxin treatment of human advanced cancer", Cancer Res., 1982, 42(5): 2054-2058.
Buzzi, et al., "CRM197 (nontoxic diphtheria toxin): effects on advanced cancer patients", Cancer Immunol. Immunother., 2004, 53: 1041-1048 (2004).
Buzzi, et al., "CRM197 and cancer: Effects of intratumoral administration", Therapy, Sep. 2004, 1(1): 61-66.
Buzzi, et al., "CRM197; Effects of intravenous administration to advanced cancer patients", American Association for Cancer Research, 2004, 64(7), Supplement.
Cheever et al, "The prioritization of cancer antigens: a national cancer institute pilot project for the acceleration of translational research", Clin Cancer Res., 2009, 15(17): 5323-5337.
Cripe et al., "Phase 1 Study of Intratumoral Pexa-Vec (JX-594), an Oncolytic and Immunotherapeutic Vaccinia Virus, in Pediatric Cancer Patients", Molecular Therapy, 2015, 23(3): 602-608.
Davis et al., "Basic Methods in Molecular Biology," 1986.
Fiorentini, et al., "Clinical experience of treatment of metastatic melanoma and solid tumours adopting a derivative of diphtheria toxin: cross-reacting material 197", In Vivo, 2013, 27(2): 197-202.
Frietze et al., "Engineering virus-like particles as vaccine platforms", Curr Opin Virol., 2016, 18: 44-49.
Geha et al., "The genetic basis of immunoglobulin-class switching", *N Engl J Med.*, 1994, 330(14): 1008-1009.
Graham et al., "A new technique for the assay of infectivity of human adenovirus 5 DNA", Virology, 1973, 52(2): 456-467.
Grossardt et al., "Granulocyte-macrophage colony-stimulating factor-armed oncolytic measles virus is an effective therapeutic cancer vaccine", Human Gene Therapy, 2013, 24: 644-654.
Haddad, "Genetically Engineered Vaccinia Viruses as Agents for Cancer Treatment, Imaging, and Transgene Delivery", Frontiers in Immunology, 2017, 7: 96.
He et al., "CCL3 and CCL20—recruited dendritic cells modified by melanoma antigen gene-1 induce anti-tumor immunity against gastric cancer ex vivo and in vivo", Journal of Experimental & Clinical Cancer Research, 2010, 29: 37.
Hirooka et al., "Comprehensive immunotherapy combined with intratumoral injection of zoledronate-pulsed dendritic cells, intravenous adoptive activated T lymphocyte and gemcitabine in unresectable locally advanced pancreatic carcinoma: a phase I/II trial", Oncotarget, 2018, 9(2): 2838-2847.
Howells et al., "Oncolytic Viruses—Interaction of Virus and Tumor Cells in the Battle to Eliminate Cancer", Front Oncol., 2017, 7: 195.
Hutzler et al., "Antigen-specific oncolytic MV-based tumor vaccines through presentation of selected tumor-associated antigens on infected cells or virus-like particles", Scientific Reports, 2017, 7: 16892.
International Search Report and Written Opinion for PCT International Application No. PCT/IB2020/053898, dated Jul. 2, 2020, 17 pages.
Jurincic-Winkler et al., "Antibody response to keyhole limpet hemocyanin (KLH) treatment in patients with superficial bladder carcinoma", *Anticancer Res.*, 1996,16(4A): 2105-2110.
Kalinski et al., "Consensual immunity: success-driven development of T-helper-1 and T-helper-2 responses", Nature Reviews, Immunology, 2005, 5: 251-260.
Koup et al., "Vaccine design for CD8 T lymphocyte responses", Cold Spring Harb Perspect Med., 2011, 1(1): a007252.
Kudo-Saito, et al., "Intratumoral vaccination and diversified subcutaneous/intratumoral vaccination with recombinant poxviruses encoding a tumor antigen and multiple costimulatory molecules", Clin Cancer Res., 2004, 10(3): 1090-1099.
Lal et al., "Recombinant viruses with other anti-cancer therapeutics: a step towards advancement of oncolytic virotherapy", Cancer Gene Ther., 2018, 25: 216-226.
Laurell et al., "Intratumorally injected pro-inflammatory allogeneic dendritic cells as immune enhancers: a first-in-human study in unfavourable risk patients with metastatic renal cell carcinoma", Journal for Immunotherapy of Cancer, 2017, 5:52.
Lawler et al., "Oncolytic Viruses in Cancer Treatment: A Review", JAMA Oncol. Review, 2017, 3(6): 841-849.
Lundstrom, "Viral Vectors in Gene Therapy", Diseases, 2018, 6(2): 42.
Malito et al., "Structural basis for lack of toxicity of the diphtheria toxin mutant CRM197", *Proc Natl Acad Sci U S A*, 2012, 109(14): 5229-5234.
Marelli et al., "Oncolytic Viral Therapy and the Immune System: A Double-Edged Sword Against Cancer", Frontiers in Immunology, 2018, 9: 866.
Mishra et al., "Structural and immunological characterization of *E. coli* derived recombinant $CRM_{197}$ protein used as carrier in conjugate vaccines", *Bioscience reports*, 2018, 38(5): BSR20180238.
Miyamoto et al., "Heparin-binding epidermal growth factor-like growth factor as a novel targeting molecule for cancer therapy", *Cancer Sci*, 2006, 97(5): 341-347.
Miyamoto, et al., "New approach to cancer therapy: heparin binding-epidermal growth factor-like growth factor as a novel targeting molecule", Anticancer Res., 2007, 27(6A): 3713-3721.
Mohan et al., "Applications of chemokines as adjuvants for vaccine immunotherapy", Immunobiology, 2018, 223(6-7): 477-485.
Moya et al., "Inhibition of coated pit formation in Hep2 cells blocks the cytotoxicity of diphtheria toxin but not that of ricin toxin", *J Cell Biol.*, 1985, 101(2): 548-559.
Nam, et al., "Anti-tumor Effect of Intravenous Administration of CRM197 for Triple-negative Breast Cancer Therapy", Anticancer Res., 2016, 36(7): 3651-3657.
Nguyen-Hoai et al., "CCL21 (SLC) improves tumor protection by a DNA vaccine in a Her2/neu mouse tumor model", Cancer Gene Therapy, 2012, 19: 69-76.
Olusanya et al., "Liposomal Drug Delivery Systems and Anticancer Drugs", Molecules, 2018, 23(4): 907.
Pashine et al., "Targeting the innate immune response with improved vaccine adjuvants", Nature Medicine Supplement, 2005, 11(4): S63-S68.
Saxena et al., "Re-emergence of Dendritic Cell Vaccines for Cancer Treatment", Trends in Cancer, 2018, 4:2: 119-137.
Stickings, et al., "Transcutaneous immunization with cross-reacting material CRM(197) of diphtheria toxin boosts functional antibody levels in mice primed parenterally with adsorbed diphtheria toxoid vaccine", Infect Immun., 2008, 76(4): 1766-1773.
Suhrbier, "Multi-epitope DNA vaccines", *Immunol Cell Biol.*, 1997, 75(4): 402-408.
Tacken et al., "Effective induction of naive and recall T-cell responses by targeting antigen to human dendritic cells via a humanized anti-DC-SIGN antibody", Blood, 2005, 106(4): 1278-1285.
Temizoz et al., "Vaccine adjuvants as potential cancer immunotherapeutics", Int Immunol., 2016, 28(7): 329-338.
Triozzi et al., "Intratumoral injection of dendritic cells derived in vitro in patients with metastatic cancer", Cancer, 2000, 89(12): 2646-2654.
Twumasi-Boateng et al., "Oncolytic viruses as engineering platforms for combination immunotherapy", Nature Reviews Cancer, 2018, 18(7): 419-432.

(56) References Cited

OTHER PUBLICATIONS

Uchida et al., "Mutation in the structural gene for diphtheria toxin carried by temperate phage", *Nat New Biol.*, 1971, 233(35): 8-11.
Ud Din et al., "Effective use of nanocarriers as drug delivery systems for the treatment of selected tumors", Int J Nanomedicine, 2017, 12: 7291-7309.
Van Nuffel et al., "Loading of dendritic cells for immunotherapy", ISBT Science Series, 2013, 8: 161-164.
Van Tendeloo et al., "Induction of complete and molecular remissions in acute myeloid leukemia by Wilms' tumor 1 antigen-targeted dendritic cell vaccination", *PNAS*, 2010, 107(31): 13824-13829.
Vigneron et al, "Database of T cell-defined human tumor antigens: the 2013 update", Cancer Immunity, 2013, 13: 15.
Wallgren et al., "Direct Allorecognition Promotes Activation of Bystander Dendritic Cells and Licenses Them for Th1 Priming: A Functional Link Between Direct and Indirect Allosensitization", Scandinavian Journal of Immunology, 2005, 62: 234-242.

```
                         SEQUENCE LISTING


<160> NUMBER OF SEQ ID NOS: 3

<210> SEQ ID NO 1
<211> LENGTH: 535
<212> TYPE: PRT
<213> ORGANISM: Corynebacterium diphtheriae

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335
```

-continued

```
Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535


<210> SEQ ID NO 2
<211> LENGTH: 151
<212> TYPE: PRT
<213> ORGANISM: Corynebacterium diphtheriae

<400> SEQUENCE: 2

Lys Thr Gln Pro Phe Leu His Asp Gly Tyr Ala Val Ser Trp Asn Thr
1               5                   10                  15

Val Glu Asp Ser Ile Ile Arg Thr Gly Phe Gln Gly Glu Ser Gly His
            20                  25                  30

Asp Ile Lys Ile Thr Ala Glu Asn Thr Pro Leu Pro Ile Ala Gly Val
        35                  40                  45

Leu Leu Pro Thr Ile Pro Gly Lys Leu Asp Val Asn Lys Ser Lys Thr
    50                  55                  60

His Ile Ser Val Asn Gly Arg Lys Ile Arg Met Arg Cys Arg Ala Ile
65                  70                  75                  80

Asp Gly Asp Val Thr Phe Cys Arg Pro Lys Ser Pro Val Tyr Val Gly
                85                  90                  95

Asn Gly Val His Ala Asn Leu His Val Ala Phe His Arg Ser Ser Ser
            100                 105                 110

Glu Lys Ile His Ser Asn Glu Ile Ser Ser Asp Ser Ile Gly Val Leu
        115                 120                 125

Gly Tyr Gln Lys Thr Val Asp His Thr Lys Val Asn Ser Lys Leu Ser
    130                 135                 140

Leu Phe Phe Glu Ile Lys Ser
145                 150


<210> SEQ ID NO 3
```

-continued

```
<211> LENGTH: 149
<212> TYPE: PRT
<213> ORGANISM: Corynebacterium diphtheriae

<400> SEQUENCE: 3

Gln Pro Phe Leu His Asp Gly Tyr Ala Val Ser Trp Asn Thr Val Glu
1               5                   10                  15

Asp Ser Ile Ile Arg Thr Gly Phe Gln Gly Glu Ser Gly His Asp Ile
            20                  25                  30

Lys Ile Thr Ala Glu Asn Thr Pro Leu Pro Ile Ala Gly Val Leu Leu
        35                  40                  45

Pro Thr Ile Pro Gly Lys Leu Asp Val Asn Lys Ser Lys Thr His Ile
    50                  55                  60

Ser Val Asn Gly Arg Lys Ile Arg Met Arg Cys Arg Ala Ile Asp Gly
65                  70                  75                  80

Asp Val Thr Phe Cys Arg Pro Lys Ser Pro Val Tyr Val Gly Asn Gly
                85                  90                  95

Val His Ala Asn Leu His Val Ala Phe His Arg Ser Ser Ser Glu Lys
            100                 105                 110

Ile His Ser Asn Glu Ile Ser Ser Asp Ser Ile Gly Val Leu Gly Tyr
        115                 120                 125

Gln Lys Thr Val Asp His Thr Lys Val Asn Ser Lys Leu Ser Leu Phe
    130                 135                 140

Phe Glu Ile Lys Ser
145
```

COMBINATION PRODUCT FOR USE IN TUMOR VACCINATION

RELATED APPLICATIONS

This application is a continuation of International Patent Application No. PCT/NL2019/050451, filed Jul. 16, 2019, which claims priority to European Patent Application Nos. 19170999.7, filed Apr. 25, 2019; and 18183694.1, filed Jul. 16, 2018, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Apr. 21, 2020, is named 700427_DCP9-004PCCON_ST25.txt and is 7,707 bytes in size.

FIELD OF THE INVENTION

The present invention is in the field of tumor immunotherapy. More specifically, the invention is in the field of pharmaceutical combinations that can be employed as therapeutic tumor vaccines. The invention is based on a novel concept in the treatment of cancer, which concept involves tumor antigen-independent vaccination. The invention relates inter alia to pharmaceutical combinations that embody such a concept.

STATE OF THE ART

Traditionally, and currently still, the focus in therapeutic tumor vaccines is on vaccination with tumor antigens, which are processed by antigen-presenting cells (APC's) such as dendritic cells (DCs) to thereby provide for T cell activation and the mounting of an immune response against the tumor.

The goal of such a vaccination strategy is to enlarge the pool of tumor-specific T-cells from the naïve repertoire, but also to reverse tumor-associated dormancy or anergy through the presentation of tumor antigens, in an effort to break central tolerance to those antigens and to overcome blunting of the $CD4^+$ and/or $CD8^+$ T cell repertoire.

The difficulty in designing therapeutic tumor vaccines, where preferentially T-cells against tumor-specific epitopes are stimulated, lies in the propensity of the tumor to evade immune control by altering itself to reduce expression of the tumor antigens or by creating an environment (the tumor micro-environment or TME) that is inhibitory for T cells and other cells of the immune system. In this way, T cell repertoires that recognize tumor antigens are inactivated, leading to inert or exhausted T cell populations. As a result, vaccination with tumor antigens will no longer mount effective T cell responses.

Current vaccination approaches are dependent on the tumor antigens expressed at a specific moment by the tumor. This means that these vaccination approaches are circumvented by the immune-evasive properties of tumor cells because the natural selection pressure on the tumor is generally not strong enough to force the tumor into cell death. Further, it remains difficult to employ tumor-specific antigens that are not also self-antigens, the latter being generally tolerized by the immune system or provide for weak T-cell-mediated immune responses. A current research focus in the field of therapeutic tumor vaccines lies in the identification of inter alia tumor neoantigens. Although these neoantigens might sufficiently stimulate T-cells following vaccination, they have an intrinsic disadvantage in that they are generally patient-specific and thus are not suitable as a tumor vaccine that finds broad application over the patient population. Also, they are not stably expressed and may alter over time, making it even more challenging to compose the correct vaccines formulations. It is clear from the above that current tumor vaccination approaches are based on vaccination with tumor antigens and are directed to the antigenic state of a tumor at a given time point, and thus do not actively manipulate the antigenic state of the tumor.

There is thus a need for improved therapeutic tumor vaccines, which are not dependent on tumor-antigen expressed by a tumor, and which incorporate antigens that provide for an optimal T-cell response upon vaccination.

The present invention fulfills in such a need, and is based on a new insight in the field of therapeutic tumor vaccines.

THE INVENTION

The present invention is based on the novel strategy in tumor vaccination also referred to as 'tumor-antigen independent vaccination'. By designing a vaccination approach that is independent from tumor antigens, an immune response is raised against an antigen that is immunogenic in a human subject and that is of foreign (non-human) origin. Such an immunogen provides for a strong immune response, for instance by activating T-cells from the naïve repertoire or by tapping into pre-existing immunity by re-activating memory T-cells and/or memory B-cells that were generated during a prior immune response that was not an immune response against the tumor, and preferably was an immune response that occurred prior to establishment of a tumor as the result of common vaccination against infectious diseases. This principle overcomes the restrictions of tumor antigen-based vaccination described above and is applicable over the entire patient population. This new vaccination concept is based on two important pillars.

The first pillar in tumor-antigen independent vaccination involves the administration of (vaccination with) an immunogenic composition (such as a vaccine composition) comprising an antigen foreign or exogenous to a human subject as an immunogen. Such an antigen is preferably highly immunogenic, and can be an antigen that is not, or is only rarely, encountered by the immune system of human subjects except via common vaccination against infectious diseases. In other words, a vaccination step is performed by using a non-human antigen that is preferably not a tumor-antigen.

The second pillar in tumor-antigen independent vaccination involves actively marking the tumor cell, or its direct or immediate environment—the tumor micro-environment (TME)—with the same antigen that was employed in the first pillar relating to vaccination. In other words, the tumor, or its direct environment—the tumor micro-environment (TME)—is manipulated by presentation of a non-human antigen that is preferably not the tumor-antigen to mark the tumor as a target for an immune response. Preferably, prior to tumor marking, such an immune response is already elicited or mounted.

This vaccination strategy is thus not dependent on vaccination with tumor-antigens such as tumor-neoantigens that are expressed at a specific time point during tumor growth and development. On the contrary, it is now possible to select any antigen that is immunogenic in a human subject, that is of foreign (non-human) origin, and that is expected to provide a strong immune response, by activating T-cells from for instance the naïve repertoire or by tapping into pre-existing immunity against antigens that are not antigens specific to the tumor of interest; and (i) to vaccinate against said antigen so as to mount the desired immune response against said antigen, and (ii) to mark the tumor as a target for such an immune response by allowing presentation of a corresponding antigen in the tumor vicinity. The step of administration of the immunogenic composition can be performed prior to or following tumor marking. It is highly preferred that such a vaccination step is performed prior to the step of tumor marking.

This novel strategy requires active interference in (or manipulation of) the antigen expression pattern of the tumor, which hitherto has not been contemplated or envisaged. This invention opens up a new field of tumor vaccine research, and multiple practical implementations of this concept are now foreseeable. Even pre-existing immune cells, such as memory T-cells and/or B-cells induced by prior infection or vaccination earlier in life, that are normally not activated by tumor antigens, can now be recruited in an immune response against a tumor by manipulating a tumor to present antigens that activate such pre-existing immune cells.

Therefore, the invention provides in a first aspect, a combination product for use in eliciting an immune response against a tumor in a subject, said product comprising:—an immunogenic composition comprising a non-human antigenic polypeptide as an immunogen, or comprising a nucleic acid encoding said immunogen, and optionally one or more pharmaceutically-acceptable carriers, adjuvants, excipients and/or diluents; and—said non-human antigenic polypeptide, or a nucleic acid encoding said polypeptide; wherein said polypeptide or said nucleic acid is prepared for intratumoral delivery.

In the same manner, the invention also provides a two part combination product for use in eliciting an immune response against a tumor in a subject, said product comprising:—a first part for generating an immune response, said first part comprising an immunogenic composition comprising a non-human antigenic polypeptide as an immunogen, or comprising a nucleic acid encoding said immunogen, and optionally one or more pharmaceutically-acceptable carriers, adjuvants, excipients and/or diluents; and—a second part for delivery to a tumor, said second part comprising said non-human antigenic polypeptide, or a nucleic acid encoding said polypeptide, in a form such that said polypeptide or said nucleic acid is prepared for intratumoral delivery.

Figure 4:
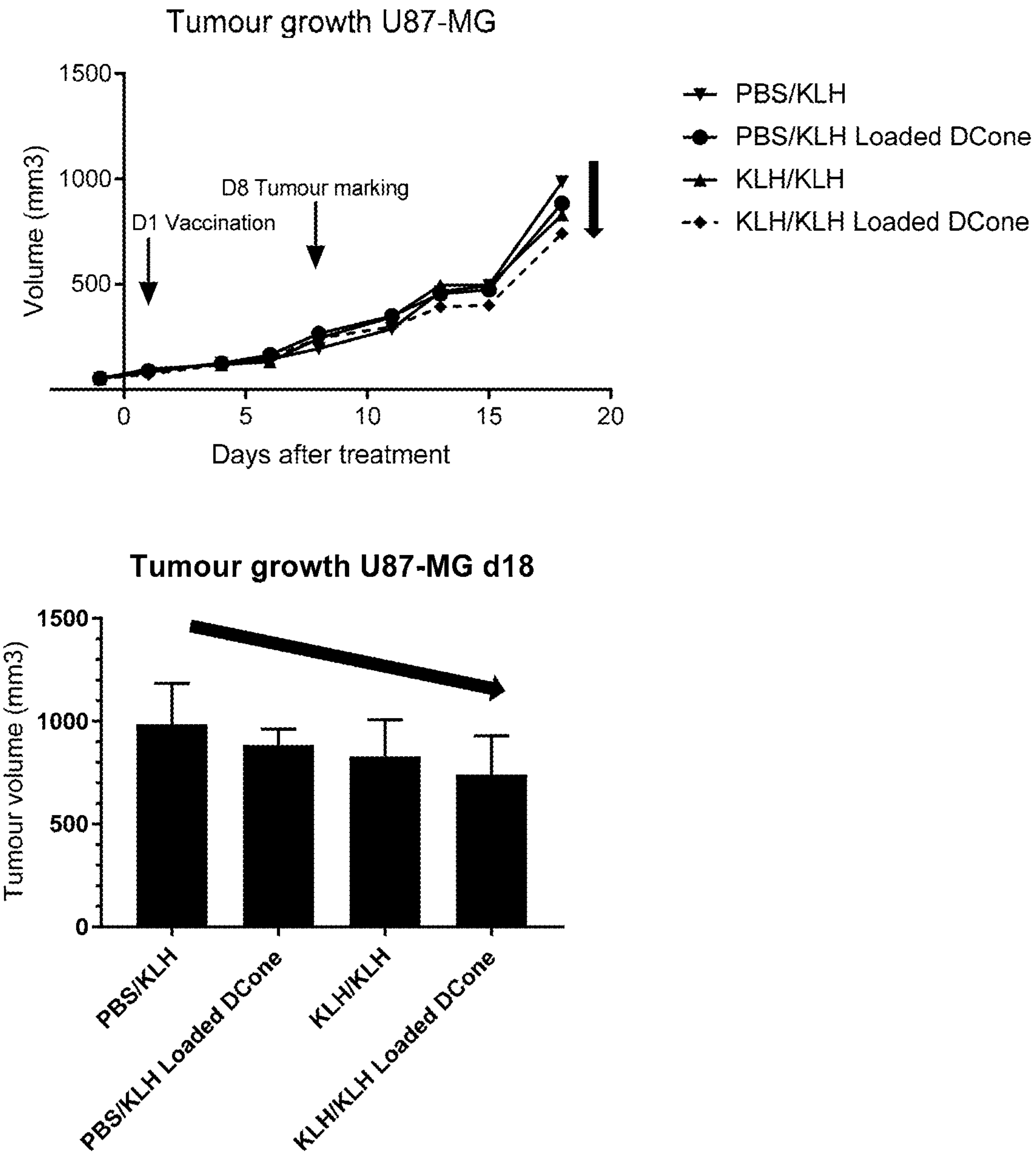
Figure 5:
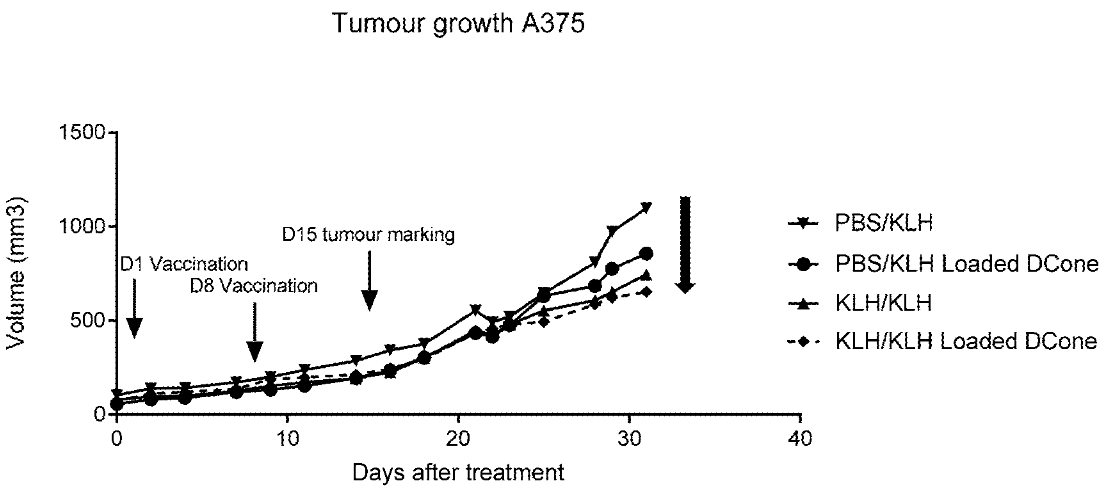
Figure 5:
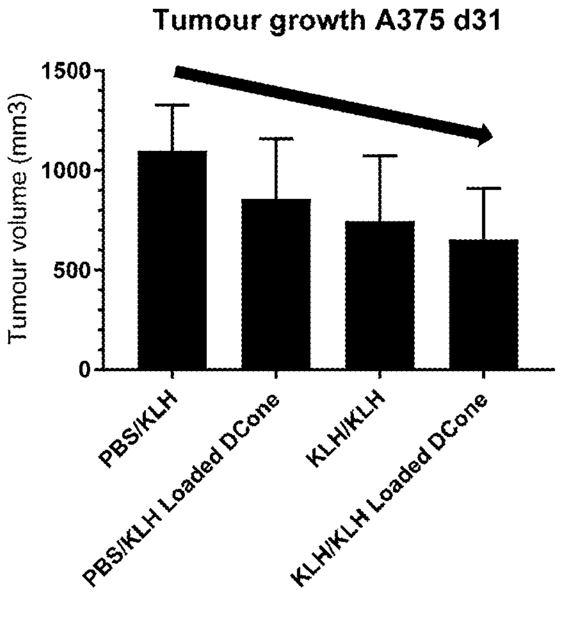

Example 2 and FIGS. 4 and 5 show that tumor growth is slowed in two different solid tumor models when a combination product for use according to the invention is employed. In addition, when DCOne dendritic cells loaded with a foreign antigen are used for tumor marking, a significantly increased T-cell mediated IgM to IgG switch is observed (Example 3 and FIGS. 6A-6B).

The term “combination product”, as used herein, refers to either a combination of products in one dosage unit form or a kit of parts for the combined administration of the products of the combination. The products of the combination may be administered together at the same time, separately of each other at the same time or separately of each other staggered in time. Simultaneous, separate and sequential administration of the products of the combination is for instance envisaged. The immunogenic composition and non-human antigenic polypeptide prepared for intratumoral delivery (also shorted as “non-human antigenic polypeptide” in instances) are described herein in the context of combination therapy, and can be administered separately. Preferably, the products of the combination are administered separately, more preferably sequentially, most preferably the immunogenic composition is administered first, and the non-human antigenic polypeptide prepared for intratumoral delivery second. Preferably the time between said administrations is such that the immune response elicited is, under the circumstances, as strong as possible. The time between said administrations can be 1-90 days, including 5-60, 10-60 or 15-40 days.

The term “immune response”, as used herein, includes T-cell mediated and/or B-cell mediated immune responses. Exemplary immune functions of T cells include, e.g., cytokine production and induction of cytotoxicity in other cells. B-cell functions include antibody production. In addition, the term includes immune responses that are indirectly affected by T-cell activation, e.g., antibody production and activation of cytokine responsive cells, e.g., macrophages. Immune cells involved in the immune response include lymphocytes, such as B cells and T cells ($CD4^+$ and $CD8^+$ cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. Preferably, the term refers to a T-cell mediated immune response. The immune response may in some embodiments be a T cell-dependent immune response. The skilled person understands that, in the context of the present invention, the phrase “immune response against a tumor” also includes immune responses against a non-human antigenic polypeptide that is introduced into the tumor micro-environment by intratumoral administration, such as intratumoral administration of (i) dendritic cells, including autologous or allogeneic dendritic cells, loaded with said polypeptide or (ii) viruses comprising a nucleic acid encoding said polypeptide.

The term “T-cell dependent immune response”, as used herein, refers to an immune response wherein either T-cells, B-cells or both T- and B-cell populations are activated, and wherein T-cells further assist T and B cells and other immune cells in executing their function.

The term “tumor”, as used herein, includes reference to cellular material, e.g. a tissue, proliferating at an abnormally high rate. A growth comprising neoplastic cells is a neoplasm, also known as a “tumor”, and generally forms a distinct tissue mass in a body of a subject. A tumor may show partial or total lack of structural organization and functional coordination with the normal tissue. As used herein, a tumor is intended to encompass hematopoietic tumors as well as solid tumors. Preferably, the tumor is a solid tumor. The term “tumor” as used herein, includes reference to the tumor micro-environment, i.e. the area within the tumor and the area directly outside the tumorous tissue, but preferably still within the boundaries of the tumor tissue, preferably the tumor interstitial compartment of a tumor, which is defined herein as all that is interposed between the plasma membrane of neoplastic cells and the vascular wall of the newly formed neovessels.

A tumor may be benign (benign tumor) or malignant (malignant tumor or cancer). Malignant tumors can be broadly classified into three major types: those arising from epithelial structures are called carcinomas, those that originate from connective tissues such as muscle, cartilage, fat or bone are called sarcomas, and those affecting hematopoietic structures (structures pertaining to the formation of blood cells) including components of the immune system, are called leukemias and lymphomas. Other tumors include, but are not limited to, neurofibromatosis. Preferably, the tumor is not a bladder tumor, more preferably not a bladder cancer, even more preferably not a resected bladder cancer.

The term "subject", as used herein, refers to the recipient of a combination product—or the components thereof—as described herein, i.e. a recipient that can mount a cellular immune response, and is a mammal, preferably a human. The terms "patient" and "subject" may be used interchangeable. The subject is preferably a human, more preferably a human suffering from a tumor.

The term "polypeptide", as used herein, refers to a molecule composed of amino acid monomers linearly linked by amide bonds (peptide bonds). As used herein, the term is mutually inclusive of the terms "peptide" and "protein" and includes reference to parts of said polypeptides.

The term "nucleic acid", as used herein, refers to DNA and RNA including mRNA or cDNA, as well as synthetic congeners thereof. The nucleic acid can be a recombinant or synthetic nucleic acid.

The term "antigen" or "antigenic", as used in relation to a polypeptide as described herein, refers generally to a biological molecule which contains at least one epitope specifically recognized by a T-cell receptor, an antibody, or other elements of specific humoral and/or cellular immunity. The whole molecule may be recognized, or one or more portions of the molecule, for instance following intracellular processing of a polypeptide into an MHC peptide antigen complex and subsequent antigen presentation. The term "antigenic polypeptide" is interchangeable with "polypeptide antigen". This terminology includes antigenic parts of said polypeptides, for instance produced after intracellular processing of a polypeptide and in the context of a MHC peptide antigen complex. The term "antigen" or "antigenic" includes reference to at least one, or more, antigenic epitopes of a polypeptide as described herein.

Furthermore, for purposes of the present invention, the term "antigen" or "antigenic" may also be used to refer to a polypeptide that includes modifications, such as deletions, additions and substitutions to the native sequence, as long as the polypeptide maintains the ability to be specifically recognized by T-cell receptors and/or antibodies following vaccination with said polypeptide as an immunogen. These modifications may be deliberate, as through site-directed mutagenesis, or through particular synthetic procedures, or through a genetic engineering approach, or may be accidental, such as through mutations of hosts, which produce the antigens. Synthetic antigens are also included, for example, polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242 3249; Suhrbier, A. (1997) *Immunol. and Cell Biol.* 75:402 408; Gardner et al. (1998) 12th World AIDS Conference, Geneva, Switzerland, Jun. 28-Jul. 3, 1998). Preferably, the antigenic polypeptide contains at least 1, 2, 3, 4, 5, 6, 7, 8, 9 or 10 $CD4^+$ T-helper cell epitope(s) and/or at least 1, 2, 3, 4, 5, 6, 7, 8, 9 or 10 $CD8^+$ cytotoxic T-cell epitope(s).

The term "immunogenic composition", as used herein, refers to a substance which induces a specific immune response against an immunogen in a subject who is in need of an immune response against said immunogen. The composition may include an adjuvant and optionally one or more pharmaceutically-acceptable carriers, excipients and/or diluents. The immunogenic composition can be employed in prime-boost vaccination, such as at least 2, 3, 4 or at least 5 immunizations separated in time. The immunogenic composition can be an (allogeneic) dendritic cell comprising said immunogen.

The term "immunogen", as used herein, refers to a compound such as a polypeptide capable of eliciting an immune response that is specifically directed against an antigenic polypeptide as described herein. In the context of the invention, an immunogen is also an antigen, i.e. an antigenic polypeptide. In contrast, an antigen is not necessarily an immunogen. In the context of the invention, the immunogen is used for vaccination (in an immunogenic composition such as a vaccine composition), and the antigenic polypeptide prepared for intratumoral delivery is instead used for marking a tumor as a target for an immune response to be elicited, or as a target for an immune response that is already elicited, in a subject. The term "immunogen" is also used to refer to a nucleic acid which encodes the non-human antigenic polypeptide as described herein. In addition, embodiments that describe the antigenic polypeptide, also apply to an immunogen as described herein.

The term "non-human", as used herein in the context of an antigenic polypeptide, includes polypeptides that are not of human origin, including a bacterial polypeptide, a polypeptide of an organism of the Archaea domain, a fungal polypeptide and a viral polypeptide. Also included are plant polypeptides and non-human mammalian polypeptides such as polypeptides of non-human primates, rodents (e.g. mice and rats), rabbits, pigs, sheep, goats, cows, pigs, horses and donkeys, and birds (e.g., chickens, turkeys, ducks, geese and the like). Also included are polypeptides of snails or other mollusks, including *Megathura crenulata*. The term also encompasses synthetic polypeptides, i.e. polypeptides that have an artificial sequence designed by man and that do not occur in nature or are not yet identified in nature. In addition, the term comprises human polypeptides comprising an amino acid alteration from the native sequence, the alteration providing for immunogenicity in a human subject.

The term "intratumoral", as used herein, refers to delivery or transport of the antigenic polypeptide, or the nucleic acid encoding said polypeptide, into the tumor. One example of intratumoral delivery, or transport, of the antigenic polypeptide as described herein is by intratumoral administration, a route of administration generally known in the art. As an alternative route for intratumoral administration, the antigen may be delivered to the tumor via a tumor-specific carrier, such as an oncolytic virus or a gene therapy vector, which have been broadly developed to deliver gene sequences to tumors. The use of such vehicles allows for multiple routes of administration—in addition to intratumoral administration —, such as intravenous or intraperitoneal administration, subsequently resulting in the delivery of the nucleic acid encoding said polypeptide, into the tumor (Lundstrom, *Diseases,* 6(2):42 (2018); Alemany, *Biomedicines,* 2, p. 36-49 (2014); Twumasi-Boateng et al., *Nature Reviews Cancer* 18, p. 419-432 (2018).

The phrase "prepared for intratumoral delivery", as used herein, refers to the fact that the antigenic polypeptide as described herein, or the nucleic acid encoding said polypeptide as described herein (not the immunogen), is adapted for intratumoral delivery, or is, in other words, in a form that allows for intratumoral delivery. The preparation used for intratumoral delivery may be composed such that it has a beneficial effect on the interaction between the immune system and the tumor. For instance, dendritic cells, such as autologous or allogeneic dendritic cells, can be loaded with said polypeptide and upon intratumoral administration may provide for additional immune stimulation via direct interaction with T cells entering the tumor and/or indirectly by recruiting bystander antigen-presenting cells (Laurell et al., *Journal for Immunotherapy of Cancer,* 5:52 (2017); Wallgren et al., *Scandinavian Journal of Immunology,* 62, p. 234-242 (2005). Another example of such preparation is that the polypeptide or nucleic acid as described herein can be comprised in a tumor-delivery vehicle such as a tumor-targeted vehicle including a tumor-specific virus such as an oncolytic virus (or any other virus that selectively replicates in tumor cells) that infects a tumor cell and which allows for (i) expression of said nucleic acid in a tumor cell, and (ii) (subsequently) intracellular processing and antigen presentation (MHC) of said (expressed) polypeptide by said tumor cell. The skilled person is well aware of other methods and means for preparing a polypeptide, or a nucleic acid encoding said polypeptide, for intratumoral delivery. For instance, the skilled person can apply other tumor-targeted delivery vehicles such as a tumor-specific nanoparticle or he can apply intratumoral administration through intratumoral injection in order to deliver said polypeptide or nucleic acid into a tumor. Preferably, the polypeptide or nucleic acid prepared for intratumoral delivery as described herein, is comprised in a tumor-targeted vehicle.

The combination product for use as described herein, is for use in eliciting an immune response specifically directed against a tumor in a subject. The skilled person understands that "specifically directed" refers to an immune response that is specific for a tumor. The specificity is introduced by a step of marking a tumor with a non-human antigenic polypeptide as a target for an immune response, and by eliciting an immune response against an antigenic part of said non-human antigenic polypeptide (i.e. the target). Thus, preferably, the combination product for use as described herein, is for use in eliciting an immune response against a tumor marked as a target for said immune response. Preferably, the combination product for use as described herein, is for use in eliciting an immune response against a tumor that is marked as a target for said immune response; wherein said target is a non-human antigenic polypeptide as described herein.

In the present invention, the non-human antigenic polypeptide, or a nucleic acid encoding said polypeptide, prepared for intratumoral delivery as described herein, serves the purpose of marking the tumor as a target for an immune response (polypeptide/nucleic acid for marking a tumor). Thus, preferably, said polypeptide or said nucleic acid prepared for intratumoral delivery marks the tumor as a target for an immune response following intratumoral delivery.

The term "marking", "mark" or "marked", as used herein, refers to active manipulation of the antigenic state of a tumor by intratumoral delivery of a antigenic polypeptide, or a nucleic acid encoding said polypeptide, as described herein. This provides for direct labelling of a tumor cell through intracellular delivery and subsequent processing and presentation of said polypeptide by said tumor cell, or provides for indirect labelling of a tumor via (i) intracellular delivery and subsequent processing and presentation of said polypeptide by a non-tumor cell in said tumor or (ii) extracellular delivery of said antigenic polypeptide to said tumor (i.e. extracellular to the cells present in said tumor before marking), for instance by using a dendritic cell that comprises a nucleic acid encoding said polypeptide or that is loaded with said antigenic polypeptide.

The immunogenic composition as described herein, which also comprises said non-human antigenic polypeptide or the nucleic acid encoding said polypeptide, but as an immunogen (polypeptide/nucleic acid for eliciting an immune response), serves the purpose of eliciting an immune response against a tumor that is marked, or to be marked, with said non-human antigenic polypeptide. Thus, preferably, said immunogen is for eliciting an immune response against a tumor that is marked, or to be marked, with said non-human antigenic polypeptide, or nucleic acid, prepared for intratumoral delivery. With the present invention, in principle any antigenic polypeptide can be introduced into a tumor to generate a new antigenic target, preferably a target that is a B-cell epitope and/or T-cell epitope recognizable by an antibody and/or T-cell receptor, respectively, when an immune response against said target is elicited following administration of an immunological composition as described herein to a subject.

The skilled person directly understands that (i) the non-human antigenic polypeptide, or a nucleic acid encoding said polypeptide, prepared for intratumoral delivery as described herein (polypeptide/nucleic acid for marking a tumor) and (ii) the non-human antigenic polypeptide, or a nucleic acid encoding said polypeptide, comprised as an immunogen in an immunogenic composition as described herein (polypeptide/nucleic acid for eliciting an immune response), are matched in that the immunogen, when administered, elicits an immune response that is directed against one or more (target) epitopes established by the polypeptide or nucleic acid for marking the tumor. Thus, for instance, the polypeptides under (i) and (ii) are immunologically matched in that a T-cell epitope and/or a B-cell epitope of the marking polypeptide in a tumor are recognized by, or are reactive with, a T-cell and/or B-cell response elicited by the polypeptide employed as an immunogen. It is thus understood that the polypeptides under (i) and (ii) are based on the same non-human antigenic polypeptide and preferably share an identical antigenic part thereof, preferably at least one B-cell and/or T-cell epitope thereof (i.e. are immunologically matched). In this manner, the elicited immune response is specifically directed to the tumor marked as a target for said immune response. Thus, the formulations of the said polypeptide used for eliciting an immune response on the one hand and tumor marking on the other hand need not be the same. In fact, the skilled person appreciates that it might be beneficial to use different formulations of the said polypeptide for vaccination and tumor marking.

Preferably, the combination product for use of the invention, is for use in eliciting a T-cell mediated immune response against a tumor in a subject. Further, preferably, the combination product for use of the invention, is for use in tumor antigen-independent vaccination. Preferably, the subject is a human subject.

The term "T-cell mediated immune response", as used herein, refers to an immune response that is T-cell driven, and where elicitation of another or further immune response is dependent on activation of T-cells. Preferably, in the present invention, the immune response is a T-cell mediated immune response/T-cell dependent immune response. The skilled person is well aware of methods and means for mounting a T-cell mediated immune response/T-cell dependent immune response, for instance through selection of an appropriate antigen of which many have been described in literature including but not limited to bacterial-, fungal-, mollusk-, snail-, insect- or plant-derived antigens to which measurable T cell responses have been documented, or by selecting an appropriate adjuvant or carrier such as a chemical adjuvant, biological adjuvant, protein, viral vaccine, dendritic cell vaccine or any other composition that can be administered as a vaccine composition (Bender et al., *J. Exp.*

*Med,* 182:1663-1671 (1995); Bennett et al., *Nature,* 393: 478-480 (1998); Kalinski and Moser, *Nature,* 5:251-260 (2005); Pashine et al., *Nature Medicine Supplement,* 11:S63-S68 (2005).

The term "tumor-specific virus", as used herein, includes reference to any virus that has the capacity to selectively replicate in tumor cells.

The term "oncolytic virus", as used herein, refers to a virus that preferentially kills tumor cells as compared to normal cells. In addition, the term refers to viruses that can be engineered to carry a nucleic acid construct encoding a polypeptide, which is to be expressed in a tumor cell after infection of said tumor cell.

The term "nanoparticle", as used herein, refers to compositions that can carry a compound of interest, such as an antigenic polypeptide as described herein, and which can be functionalized on their surface with tumor-targeting or tumor-specific moieties. Examples of nanoparticles that can be engineered to actively target tumor cells are micelles and liposomes.

The term "dendritic cell", as used herein, refers to a professional antigen presenting cell (APC) that can take up an antigen such as an antigenic polypeptide into its cell, and presents the antigen, or an immunogenic part thereof together with an MHC class I complex or MHC class II complex. The term includes both immature dendritic cells ("imDC") and mature dendritic cells ("mDC"), depending on maturity. Preferably, the dendritic cell is a mature dendritic cell. More preferably, the dendritic cell is a mature dendritic cell obtained from a cell of cell line DCOne as deposited under the conditions of the Budapest treaty with the DSMZ under accession number DSMZ ACC3189 on 15 Nov. 2012. The process of obtaining mature dendritic cells from the deposited DCOne cell line is for instance described in EP2931878B1.

The Immunogenic Composition

The first pillar of the present invention relates to the administration of (vaccination with) an immunogenic composition comprising a non-human antigenic polypeptide as an immunogen, or comprising a nucleic acid encoding said immunogen, which composition may optionally comprise one or more pharmaceutically-acceptable carriers, adjuvants, excipients and/or diluents.

It is important to understand that the non-human antigenic polypeptide used in the present invention serves two purposes. The first purpose is in generating an immune response, preferably a T-cell mediated immune response, against said polypeptide, by being incorporated in an immunogenic composition as an immunogen. The second purpose is in marking a tumor as a target for said immune response. The skilled person will directly understand that it is necessary that the tumor marking and mounting/generation of an immune response are matched in that the mounted immune response is directed against the tumor thus marked. "Matched" means that the immune response (to be) elicited is specifically directed against the antigenic polypeptide actively introduced into the tumor. Preferably, the same or a corresponding antigenic epitope is used in marking the tumor and in elicitation of an immune response. Therefore, preferably following the administration of an immunogenic composition as described herein to a subject, an immune response is elicited that is specifically directed against a tumor that is to be marked (or a tumor that is already marked) as a target for an immune response based on the same antigen.

In other words, the antigenic polypeptide for marking, and the immunogen in said immunogenic composition are matched, in that the immune response that is elicited following administration of the immunogenic composition to a subject is directed against a tumor marked with said antigenic polypeptide following intratumoral delivery of the same, or at least immunogenically the same, antigenic polypeptide. More specifically, this preferably means that the immune response elicited following administration of an immunogenic composition as described herein, is specifically directed to at least one T-cell epitope and/or B-cell epitope with which the tumor is to be marked (or is marked). Preferably, the non-human antigenic polypeptide in said immunogenic composition is a polypeptide corresponding to the polypeptide used for tumor marking as described herein.

Preferably, the immune response elicited following administration of an immunogenic composition as described herein, is a T-cell mediated immune response or a T-cell-dependent immune response. It is within the skilled person's capabilities to identify appropriate immunogens and/or adjuvants that activate the cellular arm of immunity. References that aid the skilled person in selecting appropriate antigens are for instance Bender et al., *J. Exp. Med,* 182:1663-1671 (1995); Bennett et al., *Nature,* 393:478-480 (1998); Kalinski and Moser, *Nature,* 5:251-260 (2005); Van Tenderloo et al., *PNAS,* 107:31, p. 13824-13829 (2010); Anguille et al., Blood, 12; 130(15):1713-1721 (2017); Tacken et al., Blood, 106:4, p. 1278-1285 (2005); Vigneron et al, Cancer Immunity, 13:15 (2013); and Cheever et al, Clin Cancer Res; 15:5323-5337 (2009). The skilled person directly understands that antigenic polypeptides described in relation to immunogenic compositions stand also in relation to intratumoral delivery aspects, and vice versa. Examples of suitable antigens include proteins of viral, bacterial, fungal origin; allergens, toxins and venoms, or model antigens of various sources such as chicken egg ovalbumin and keyhole limpet hemocyanin from the giant keyhole limpet, *Megathura crenulata*. Other suitable antigenic polypeptides are polypeptides employed in a prior vaccination of a subject, such as recall antigens, which are described in more detail herein below. Common vaccines, used in such vaccinations, may include different antigenic polypeptides, which can be multivalent in that they comprise different microbial (recall) antigens with or without adjuvants. The term "recall antigen", as used herein, refers to an antigenic polypeptide which has previously (before occurrence of a tumor) been encountered by a subject, preferably via vaccination and for which there is pre-existing immunity in said subject. References that aid the skilled person in selecting adjuvants that direct the immune response towards cellular immunity are for instance Pashine et al., *Nature Medicine Supplement,* 11:S63-S68 (2005) and Awate et al., Frontiers in Immunology, 4:114, p. 1-10 (2013). Examples of such adjuvants are aluminum mineral salts, oil-in-water emulsions, liposomes, toll-like receptor agonists or combinations thereof. Other adjuvants include liposomes, virosomes, MF59, Montanide, ISCOMs, QS-21, aluminum, ASO4, Poly I:C, MPL, GLA, imiquimod, CpG ODN, chitin, chitosan, ß-glucan, or combinations thereof. (Temizoz et al. *Int Immunol.* 2016 July; 28(7): 329-338).

The skilled person has multiple methods and means at his disposal that he can routinely apply in order to provide mounting of an immune response against a non-human antigenic polypeptide as an immunogen comprised in an immunogenic composition as described herein. Preferably, in a combination product for use according to the invention, said immunogenic composition comprises:—a dendritic cell comprising said immunogen or a nucleic acid encoding said immunogen; —a T-cell immune response-eliciting adjuvant;

a—a T-cell immune response-eliciting virus or a virus-like particle comprising said immunogen or a nucleic acid encoding said immunogen; or—a combination thereof.

In general, it is explicitly envisaged herein that embodiments that relate to the combination product for use according to the invention, also apply to aspects of the invention that are for instance the (i) non-human antigenic polypeptide, or nucleic acid, for use according to the invention, (ii) immunogenic composition for use according to the invention, (iii) a method for eliciting an immune response according to the invention, (iv) a method of treatment according to the invention, and other aspects of the invention where appropriate.

A preferred example of an immunogenic composition that the skilled person may employ comprises a dendritic cell comprising a non-human antigenic polypeptide as an immunogen, or a nucleic acid encoding said immunogen. It is commonly known that dendritic cells can be employed as a dendritic cell vaccine, provided that such cells are loaded with an immunogen as described herein. A preferred immunogenic composition comprises a mature dendritic cell obtained from a cell of cell line DCOne as deposited at the DSMZ under accession number DSMZ ACC3189 on 15 Nov. 2012, said mature dendritic cell comprising an antigenic polypeptide (as described herein) as an immunogen, or comprising a nucleic acid encoding said immunogen. Loading strategies for dendritic cells are discussed below. The skilled person has ample guidance on how dendritic cells can be effectively used in the form of immunogenic compositions, which is for instance described in multiple references including EP2931878 B1, WO 2014/006058 A1 and Saxena and Bhardwaj, Trends in Cancer, 4:2, p. 119-137 (2018).

Therefore, preferably, in a product for use according to the invention, the immunogenic composition comprises a dendritic cell comprising said polypeptide or a nucleic acid encoding said polypeptide, preferably wherein said dendritic cell is a mature dendritic cell obtained from a cell of cell line DCOne as deposited at the DSMZ under accession number DSMZ ACC3189 on 15 Nov. 2012.

Administration of an immunogenic composition comprising a dendritic cell as described herein is preferably through the parenteral route, which includes intravenous, intra-arterial, subcutaneous, intradermal, intranodal, intralymphatic and intramuscular administration, which are all well known to the person skilled in the art. In the context of administration of an immunogenic composition comprising a dendritic cell as described herein, the administration is not intratumoral, but instead is extratumoral and is preferably intradermal, intravenous, intranodal or intralymphatic, more preferably intradermal, intravenous or a combination thereof. The administration of an immunogenic composition comprising a dendritic cell as described herein is preferably such that an, under the circumstances, optimal T-cell mediated immune response is elicited. An optimal T-cell mediated immune response is for instance a T-cell mediated immune response that is higher than a comparable response using a different route of administration, dose, adjuvant and/or antigen.

Preferably, a pharmaceutically effective amount of an immunogenic composition comprising a dendritic cell is administered. This is an amount that is sufficient to induce an immune response against said immunogen comprised in said dendritic cell, and also against a tumor to be marked (or marked) with a corresponding antigenic polypeptide as described herein.

An immunogenic composition as described herein may further comprise a T-cell immune response-eliciting adjuvant. The term "T-cell immune response-eliciting", as used in relation to adjuvants or virus or virus-like particles herein, refers to enhancing CD4+ and/or CD8+ T-cell immune responses or driving the immune response towards CD4+ and/or CD8+ T-cell activation. The skilled person is well aware of adjuvants that can be employed for this purpose, such as liposomes, virosomes, MF59, Montanide, ISCOMs, QS-21, aluminum, AS04, Poly I:C, MPL, GLA, imiquimod, CpG ODN, chitin, chitosan, ß-glucan, or combinations thereof. (Temizoz et al. *Int Immunol.* 2016 July; 28(7): 329-338.).

An immunogenic composition as described herein may also comprise a T-cell immune response-eliciting virus, or a virus-like particle (VLP), comprising said immunogen or a nucleic acid encoding said immunogen. It is within routine experimentation to design and produce a virus or VLP that can be employed in or as an immunogenic composition as described herein. Such viruses, especially T-cell immune response-eliciting viruses or VLPs, have been described extensively for vaccination purposes. This follows for instance from Frietze et al., Curr Opin Virol., 18: 44-49 (2016); Koup and Douek, *Cold Spring Harb Perspect Med,* 2011; 1:a007252. Examples of T-cell immune response-eliciting viruses or VLPs are for instance cowpox (vaccinia) viruses or derivatives thereof such as Modified Vaccinia virus Ankara (MVA), adenovirus or adeno-associated viruses and VLP's based on human papillomavirus, hepatitis B virus or VLP's engineered to present different tumor antigens.

Administration of an immunogenic composition comprising a virus or a virus-like particle as described herein is preferably through the parenteral route, which includes intravenous, intra-arterial, subcutaneous, intradermal and intramuscular administration, which are all well known to the person skilled in the art. Such an administration is not intratumoral, but instead is extratumoral and is preferably intramuscular or subcutaneous, more preferably subcutaneous. The administration of an immunogenic composition comprising a virus or a virus-like particle as described herein is preferably such that an, under the circumstances, optimal T-cell mediated immune response is elicited. The skilled person is well aware how to elicit optimal T-cell mediated immune responses in this context, for instance by optimizing the combination of virus/VLP, antigen, adjuvant and route of administration. An optimal T-cell mediated immune response is for instance a T-cell mediated immune response that is higher than a comparable response using a different route of administration, dose, adjuvant, antigen and/or virus/VLP.

Preferably, a pharmaceutically effective amount of an immunogenic composition comprising a virus or virus-like particle is administered. This is an amount that is sufficient to induce an immune response against said immunogen comprised in a virus or VLP, and also against a tumor marked with a corresponding antigenic polypeptide as described herein.

The skilled person is aware of other suitable immunogenic compositions that mount an immune response against an immunogen as described herein. For instance, other options involve the use of a subunit vaccine comprising an immunogen as described herein, and carrier proteins coupled to an immunogen.

The Polypeptide Prepared for Intratumoral Delivery

Preferably, in the combination product for use of the invention, the polypeptide prepared for intratumoral delivery, or said nucleic acid construct encoding said polypeptide, is either tumor-targeted or is for intratumoral administration. The skilled person will understand that the new concept of tumor antigen-independent vaccination can be realized with multiple methods and means known in the art, both with regard to the marking of a tumor, as well as with the vaccination that mounts an immune response against a marked tumor as already described.

In the medical methods described herein, marking or labelling of a tumor as a target for an immune response by employing a non-human antigenic polypeptide as described herein, occurs in vivo, not in vitro or ex vivo.

More specifically, the antigenic polypeptide or nucleic acid as described herein can be prepared for intratumoral delivery in a variety of ways, generally well known in the art. For instance, preparing may involve tumor-targeting of said polypeptide or nucleic acid, e.g. by preparing a tumor-targeting composition comprising said polypeptide or nucleic acid. A tumor-targeting composition comprises the polypeptide or nucleic acid in such a way that it is rendered tumor-specific. The advantage of tumor-targeting is that, upon administration of a tumor-targeted polypeptide or nucleic acid to a subject, intratumoral delivery is effectuated on the basis of specificity for tumor tissue as compared to non-tumor tissue. Tumor specific also indicates that it may allow for homing to a tumor so as to provide for intratumoral delivery.

Preferably, in the combination product for use according to the invention, the polypeptide prepared for intratumoral delivery, or the nucleic acid encoding said polypeptide, is tumor-targeted by using one or more of: —a tumor-specific virus, including an oncolytic virus, comprising a nucleic acid encoding said polypeptide; —a tumor-specific nanoparticle comprising said polypeptide or a nucleic acid encoding said polypeptide. Alternatively, said polypeptide or nucleic acid is tumor-targeted by using a tumor-targeting antibody, peptide, small molecule, or nucleic acid aptamer fused to said polypeptide or nucleic acid.

One preferred way of tumor-targeting a polypeptide as described herein involves the use of a diphtheria toxin, which term includes detoxified variants thereof such as cross-reacting material (CRM)-197. Diphtheria toxin contains a C-terminal receptor-binding (R) domain that interacts with the heparin-binding epidermal growth factor-like precursor (HB-EGF), which is a receptor for diphtheria toxin (see for instance Mishra et al., *Bioscience Reports* (2018) 38 BSR20180238; Malito et al., *PNAS,* 109:14, p. 5229-5234 (2012); Bell et al., *Biochemistry* 1997, 36, 481-488). This receptor is expressed on different types of tumor cells. Following binding of diphtheria toxin to said receptor, the toxin is internalized though receptor-mediated endocytosis and subsequently processed into a MHC peptide antigen complex. Therefore, said receptor-binding domain allows for intratumoral (and intracellular) delivery of diphtheria toxin, and of other antigenic polypeptides described herein that are linked to the receptor-binding (R) domain of diphtheria toxin. Diphtheria toxins, diphtheria toxin-based fusion proteins and diphtheria toxin-based protein conjugates that can beneficially be employed in tumor marking are described herein below.

Another way of tumor-targeting a polypeptide or nucleic acid as described herein (so as to effectuate intratumoral delivery upon administration to a subject) involves the preparation of an oncolytic virus that comprises a nucleic acid encoding an antigenic polypeptide as described herein, which is engineered to express said nucleic acid into a tumor cell. That oncolytic viruses can be used to specifically target tumor cells is extensively described in the art, for instance in Lawler et al., *JAMA Oncol.* 1; 3(6):841-849 (2017); Howells et al., *Front Oncol.* 7:195 (2017). In addition, as exemplified in for instance WO2014138314 A1, oncolytic viruses can be modified to engage tumor cells. It is also well-known in the art that oncolytic viruses can be used to deliver a nucleic acid construct encoding a polypeptide into a tumor cell, said virus being engineered to express said polypeptide into a tumor cell (Hutzler et al., *Scientific Reports,* 7: 16892 (2017); Grossardt et al., Human Gene Therapy, 24:644-654 (2013); Andtbacka et al., Journal of Clinical Oncology, 22:25, p. 2780-2788 (2015)). Subsequent intracellular processing of said polypeptide and antigen-presentation by said tumor cell provide for a tumor marked with an antigenic polypeptide as described herein. In other words, and preferably, following intratumoral delivery an antigenic polypeptide as described herein is presented by the MHC system of a tumor cell upon expression of said nucleic acid as described herein in a cell of said tumor to thereby mark said tumor as a target for an immune response.

Examples of oncolytic viruses that can be used for tumor-targeting in the context of this invention are Adenovirus, Herpes simplex virus, Pox virus, Coxsackie virus, Maraba virus, Poliovirus, Measles virus, Newcastle Disease virus (Lal and Rajala, Cancer Gene Therapy, DOI 10.1038/s41417-018-0018-1 (2018); Haddad, Frontiers in Immunology, 7:96 (2017); Bommareddy et al., Nature Reviews Immunology (2018).

A tumor-specific virus such as an oncoloytic virus is preferably prepared in a pharmaceutical formulation adapted for parenteral administration. Such a formulation generally comprises a carrier such as for instance an aqueous or oily solution, dispersion, emulsion and/or suspension. Parenteral administration involves the injection or infusion into a body tissue or body fluid, whereby preferably a syringe, needle, or catheter is used. Preferably, the carrier is an aqueous solution, preferably distilled sterile water, saline, buffered saline, or another pharmaceutically acceptable excipient for injection. Examples of parenteral modes of administration are intravenous, intra-arterial, intra-peritoneal, subcutaneous, intramuscular and intratumoral administration, which are well known to the person skilled in the art. A preferred mode of administration of a tumor-specific virus such as an oncoloytic virus is intravenous or intratumoral administration (Marelli et al., *Frontiers in Immunology,* 9:866 (2018).

The dose to be administered of a tumor-specific virus such as an oncoloytic virus is a pharmaceutically effective dose, i.e. a dose sufficient to deliver an antigenic polypeptide or nucleic acid as described herein into a tumor. It is routine practice to determine a dosing regimen for a tumor-specific virus.

An alternative way of tumor-targeting a polypeptide or nucleic acid as described herein (so as to effectuate intratumoral delivery upon administration to a subject), involves the preparation of a tumor-specific nanoparticle comprising an antigenic polypeptide or nucleic acid as described herein, the latter being engineered to express said nucleic acid in a tumor cell after delivery. In the field of cancer therapy, it is well known that a nanoparticle, which comprises a nanocarrier loaded or combined with for instance a polypeptide of interest, are extensively described in relation to specifically/selectively targeting (homing to) tumor cells and to subsequently deliver for instance a medicament such as a polypeptide to said tumor cell. Methods and means for tumor-targeting of nanoparticles or nanocarriers is generally known and is inter alia described in Olusanya et al., *Molecules* 23:907 (2018); Din et al., *Int J Nanomedicine,*

12:7291-7309 (2017); Alibakhshi et al., *J Control Release,* 268:323-334 (2017); and US 2013/0330399 A1.

The nanoparticle, or nanocarrier as main part of the nanoparticle, can be a polymeric nanoparticle, a micelle, a liposome, a nanogel or a carbon nanotube. Such a particle or carrier can be loaded with a compound of interest (such as a polypeptide) and actively targeted to a tumor by decorating such a particle or carrier with for instance antibodies or antibody fragments specific for a tumor antigen expressed on the surface of a tumor cell (see also the aforementioned references). Tumor-targeting moieties for a nanoparticle can in principle be any biological or chemical structure that displays affinity for a molecule expressed on a tumor cell, such as a peptide, oligopeptide or polypeptide, a protein, a hormone, a vitamin, an enzyme, a ligand of a tumor antigen or an antibody or antibody fragment that specifically binds to a tumor antigen. Preferably, after administration of a tumor-targeted nanoparticle and subsequent homing and binding to a tumor cell, receptor-mediated endocytosis (internalization) allows for uptake of a nanocarrier by a tumor cell, thereby providing intracellular delivery of for instance a polypeptide of interest, which can be intracellularly processed and subsequently presented as an antigen in an MHC complex by a tumor cell.

Alternatively, after administration of a tumor-targeted nanoparticle and subsequent homing to a tumor and binding to a non-tumorous cell in the tumor, including an immune cell, such as a phagocytic cell or fibroblast, receptor-mediated endocytosis (internalization) allows for uptake of a nanocarrier by said cell, thereby providing intracellular delivery of for instance a polypeptide of interest in a tumor, which can be intracellularly processed and subsequently presented as an antigen in an MHC complex by said cell in said tumor. Specific examples of tumor-specific (or tumor-targeted) nanoparticles that can be employed for intratumoral delivery of an antigenic polypeptide or nucleic acid as described herein, are for instance poly(propylene) sulfide (PPS) nanoparticles, gold nanoparticles, PLGA nanoparticles, artificial exosomes, micelles or dendrimers.

A tumor-specific nanoparticle as described herein is preferably prepared in a pharmaceutical formulation adapted for parenteral administration. Such a formulation generally comprises a carrier such as for instance an aqueous or oily solution, dispersion, emulsion and/or suspension. Parenteral administration involves the injection or infusion into a body tissue or body fluid, whereby preferably a syringe, needle, or catheter is used. Preferably, the carrier is an aqueous solution, preferably distilled sterile water, saline, buffered saline, or another pharmaceutically acceptable excipient for injection. Examples of parenteral modes of administration are intravenous, intra-arterial, intra-peritoneal, subcutaneous, intramuscular and intratumoral administration, which are well known to the person skilled in the art. A preferred mode of administration of a tumor-specific nanoparticle is intravenous or intratumoral administration.

The dose of tumor-specific nanoparticle to be administered is a pharmaceutically effective dose, i.e. a dose sufficient to deliver an antigenic polypeptide or nucleic acid as described herein into a tumor. For a skilled person, it is routine practice to determine a dosing regimen for a tumor-specific nanoparticle.

Alternatively, in the combination product for use according to the invention, the polypeptide prepared for intratumoral delivery, or said nucleic acid encoding said polypeptide, is for intratumoral administration, preferably intratumoral injection, and is selected from:—a dendritic cell comprising said polypeptide or a nucleic acid encoding said polypeptide; and/or—an aqueous suspension or solution comprising said polypeptide. Alternatively, when said polypeptide prepared for intratumoral delivery, or said nucleic acid encoding said polypeptide, is for intratumoral administration, said polypeptide or said nucleic acid can be prepared as a virus comprising said nucleic acid, preferably wherein said virus is not necessarily tumor-specific, or wherein said nucleic acid is prepared as naked DNA, mRNA, or wherein said polypeptide or nucleic acid is in a liposome.

In embodiments where the antigenic polypeptide or the nucleic acid as described herein is not tumor-targeted, they are prepared for intratumoral delivery by being in a form that allows for intratumoral injection. The skilled person directly understands that tumor-targeted compositions as described herein can also be administered intratumorally. The skilled person is aware of pharmaceutical formulations that are adapted for intratumoral injection, which may comprise a carrier such as for instance an aqueous or oily solution, dispersion, emulsion and/or suspensions. In embodiments where the antigenic polypeptide or nucleic acid as described herein are not tumor-targeted, the antigenic polypeptide and/or nucleic acid are preferably comprised in a dendritic cell, or the antigenic polypeptide is in an aqueous suspension or solution. In the same manner, in embodiments where the antigenic polypeptide or nucleic acid as described herein are not tumor-targeted, the antigenic polypeptide and/or nucleic acid can be comprised in a virus. It is thus explicitly envisaged herein that marking of a tumor with an antigenic polypeptide can occur at a tumor cell, but does not necessarily require intracellular processing and antigen presentation by a tumor cell itself. For instance, such intracellular processing can also be effectuated by other cell types in the tumor, including immune cells such as phagocytic cells—of which macrophages are an example—or fibroblasts. When dendritic cells are employed for tumor marking, marking of a tumor can be performed by antigen processing through the MHC system of the dendritic cell itself which dendritic cell is intratumorally injected. It is also known that dendritic cells, in particular allogeneic dendritic cells, may attract endogenous immune cells including NK cells and cross-prime dendritic cells which enforces the immune response in the tumor (Laurell et al. 2017, J for Immunother. Of Cancer 5: 52).

Without being bound by theory, recruitment of previously 'untouched' immune cells into the tumor, or using pre-existing immunity that was—before tumor marking—not directed against a tumor, breaks immune tolerance resulting in further recruitment of immune cells directed against i.a. tumor antigens of the tumor.

With regard to tumor marking, the skilled person is well aware of methods and means relating to loading of dendritic cells with an antigenic polypeptide or with a nucleic acid, such as mRNA, encoding such a polypeptide. See for instance Van Nuffel et al., *ISBT Science Series,* 8, 161-164 (2013); WO 2014/006058 A1; WO 2009/034172 A1. In addition, the skilled person is well aware of methods and means for intratumoral injection of dendritic cells. See for instance US 2004/0057935 A1; Cripe et al., Molecular Therapy, 23: 3, p. 602-608 (2015); Hirooka et al., Oncotarget, 9:2, p. 2838-2847 (2018); Triozzi et al., Cancer, 89:12, p. 2646-2654 (2000); Laurell et al., *Journal for Immuno-Therapy of Cancer,* 5:52 (2017). Preferably, said polypeptide prepared for intratumoral delivery, or said nucleic acid encoding said polypeptide, is for intratumoral administration and is in the form of a dendritic cell, preferably a (mature) dendritic cell obtained from a cell of cell line DCOne as described herein, comprising said polypeptide or said nucleic acid encoding said polypeptide as described herein. A person skilled in the art can routinely define a dosing regimen that suits intratumoral administration of a dendritic cell comprising an antigenic polypeptide or a nucleic acid encoding said polypeptide (such as an mRNA) as described herein. The same applies to an aqueous suspension or solution comprising an antigenic polypeptide as described herein.

It is clear that tumor marking can be effectuated via multiple different methods and means, as long as the tumor is marked with an antigenic polypeptide as described herein. For instance, tumor marking does not have to be effectuated exclusively by intracellular processing of antigenic polypeptides by tumor cells or other cell types in the tumor. It is also possible that the antigenic polypeptides prepared for intratumoral delivery are extracellular in the tumor and are thus not internalized by cells in said tumor. The presence of an extracellular antigenic polypeptide in the tumor will attract immune cells activated prior to marking by a vaccination step as described herein. It is preferred that such a vaccination step, and subsequent generation of immunity, is performed prior to tumor marking.

Further, the polypeptide, or nucleic acid encoding said polypeptide, prepared for intratumoral delivery are preferably accompanied by immuno-modulatory compounds, such as a chemokine and/or cytokine, that modulates the tumor, preferably the TME, to increase susceptibility to an immune response, preferably to convert at least partially an immuno-tolerant tumor environment into an immuno-sensitive tumor environment or to facilitate (optimal) T-cell functionality in the TME. Such an immunomodulatory compound is preferably included in an tumor-specific virus, tumor-specific nano-particle, dendritic cell, or aqueous suspension or solution as described herein, either in the form of a polypeptide, or as a nucleic acid encoding such an polypeptide. Preferred examples of such immunomodulatory compounds are e.g. GM-CSF, CCR5, XCL1, CCL20 and CCL21 (Mohan et al., Immunobiology, 223:477-485 (2018); He et al., Journal of Experimental & Clinical Cancer Research, 29:37 (2010); Nguyen-Hoai et al., Cancer Gene Therapy, 19: 69-76 (2012). Thus, in the combination product for use according to the invention, said non-human antigenic polypeptide, or a nucleic acid encoding said polypeptide, prepared for intratumoral delivery is in a composition that also comprises an immuno-modulatory compound (such as an immuno-modulatory polypeptide or a nucleic acid encoding said immunomodulatory polypeptide), that converts at least partially an immuno-tolerant tumor microenvironment (TME) into an immuno-sensitive TME, and/or facilitates T-cell functionality in the TME. Preferably, said immuno-modulatory compound is an immunomodulatory polypeptide, or a nucleic acid encoding said immuno-modulatory polypeptide, preferably wherein said immuno-modulatory polypeptide is, or encodes for, GM-CSF, CCR5, XCL1 or CCL20, more preferably human GM-CSF, CCR5, XCL1 or CCL20. Preferably, such an immuno-modulatory compound facilitates T-cell functionality in the TME.

The term "immuno-tolerant TME", as used herein, refers to a well-established phenomenon wherein the environment within a tumor provides for tolerance of, or insensitivity to, an antitumor immune response. Preferably, a TME is immuno-tolerant if it is more tolerant of, or more insensitive to, an immune response directed against a tumor in said TME, as compared to an immune response directed against a target in an environment outside said tumor, such as for instance an environment in or near healthy cells or healthy tissue.

The term "immuno-sensitive TME", as used herein, refers to a situation wherein a tumor is sensitive or susceptible to an antitumor immune response.

With regard to the antigenic polypeptide and corresponding immunogen, in a combination product for use according to the invention, it is an embodiment of this invention that the polypeptide is not a tumor antigen. The term "tumor antigen", as used herein, includes both tumor associated antigens (TAAs) and tumor specific antigens (TSAs), including tumor neo-antigens. A tumor associated antigen is an antigen that is expressed on the surface of a tumor cell in higher amounts than is observed on normal cells or an antigen that is expressed on normal cells during fetal development. A tumor specific antigen is an antigen that is unique to tumor cells and is not expressed on normal cells. The term tumor antigen includes TAAs or TSAs that have been already identified and those that have yet to be identified.

In principle, in the context of the invention, any antigenic polypeptide can be employed insofar it is immunogenic in a human subject. This includes both antigenic polypeptides of human and non-human origin. Therefore, an antigenic polypeptide can be a human or non-human antigenic polypeptide that is immunogenic in a human subject. It is highly preferred that the antigenic polypeptide is non-human. It is nonetheless explicitly envisaged herein that in aspects and/or embodiments that recite the term "non-human antigenic polypeptide", that aspect or embodiment can be amended so as to refer to "human antigenic polypeptide", or the term "human antigenic polypeptide" can be added in such aspects and/or embodiments. Human antigenic polypeptides that are immunogenic in a human subject are for instance embryonic, ovarian or testis polypeptides. This applies for instance to NY-ESO-1, WT-1 and the MAGE antigens (see for instance Cheever et al, Clin Cancer Res; 15:5323-5337 (2009); Vigneron et al, Cancer Immunity, 13:15 (2013)). For these reasons, the invention also provides a combination product for use in eliciting an immune response against a tumor in a subject, said product comprising:

an immunogenic composition comprising an antigenic polypeptide (preferably a human or non-human antigenic polypeptide) as an immunogen, or comprising a nucleic acid encoding said immunogen, and optionally one or more pharmaceutically-acceptable carriers, adjuvants, excipients and/or diluents; and—said antigenic polypeptide (preferably human or non-human), or a nucleic acid encoding said polypeptide; wherein said polypeptide or said nucleic acid is prepared for intratumoral delivery.

An important aspect of the invention is that the non-human antigenic polypeptides that are to be employed as the immunogen and marker in aspects of this invention are not previously encountered by a subject as part of an immune response against a tumor. As indicated, the antigenic polypeptides are preferably not tumor-antigens. They can be antigens that have not previously been encountered by the immune system of the subject and to which a subject is thus immunologically naïve, or they can be antigenic polypeptides previously encountered by a subject, but not as part of an immune response against a tumor, and preferably for which protective immunity (memory T-cells and/or B-cells) exists. The latter can be highly beneficial, since it is not necessary to mount a de novo immune response, which takes time to mount, but instead taps into—or re-activates—existing immunity and directs it to a tumor according the principle mechanism of the present invention. Therefore, in one embodiment, an non-human antigenic polypeptide as described herein is rarely if ever encountered (by the immune system) by a large portion of the human population intended for potential vaccination or is an antigenic polypeptide against which immunity pre-exists (is present in a subject), wherein said immunity is not directed against a tumor. The latter form of immunity can for instance be provided by a prior vaccination against an infectious disease earlier in life, including vaccination against hepatitis, such as hepatitis A and/or B, diphtheria, tetanus, pertussis, influenza, *Haemophilus influenzae* type b, polio (poliomyelitis), measles, mumps, rubella, varicella, human papillomavirus, *Streptococcus pneumoniae* (pneumonia), *Neisseria meningitides* (meningitis) or rotaviruses (rotaviral infection). Explicitly envisaged herein as non-human antigenic polypeptides for use according to the invention are immunogenic polypeptides of one or more of hepatitis, including hepatitis A and/or B, diphtheria, tetanus, pertussis, influenza, *Haemophilus influenzae* type b, polio, measles, mumps, rubella, varicella, human papillomavirus, *Streptococcus pneumoniae, Neisseria meningitides* or rotaviruses. A non-human antigen polypeptide as described herein is preferably a microbial polypeptide employed in a prior vaccination of said subject, preferably wherein said prior vaccination was against an infectious disease, more preferably wherein said prior vaccination was against hepatitis A and/or B; diphtheria; tetanus; pertussis; influenza; *Haemophilus influenzae* type b; polio; measles; mumps; rubella; varicella; human papillomavirus, *Streptococcus pneumoniae, Neisseria meningitides* or rotaviruses. The skilled person understands that the polypeptide employed in a prior vaccination could be administered in different forms, such as part of (i) subunit vaccine, (ii) inactivated or attenuated micro-organism, (iii) toxoid vaccine (i.e. vaccine comprising inactivated toxins), etc.

More specifically, a non-human antigenic polypeptide as described herein is preferably a polypeptide selected from the group formed by VP3 from hepatitis A virus, including VP3 as identified in UniProtKB Acc. No. P08617, last modified: Aug. 1, 1988—v1; tetanus toxin from *Clostridium tetani*, including tetanus toxin as identified in UniProtKB Acc. No. P04958, last modified Jan. 23, 2007—v2; pertussis toxin from *Bordetella pertussis*, including pertussis toxin as identified in UniProtKB Acc. No. P04977, last modified: Aug. 13, 1987—v1; protein D from *Haemophilus influenzae*, including protein D as identified in UniprotKb Acc. No. R4R7Q5 (last modified: Jul. 24, 2013—v1); Vp1 capsid protein from poliovirus, including Vp1 capsid protein as identified in UniProtKB Acc. No. P03300, last modified: Jan. 23, 2007—v3; hemagglutinin from measles virus, including hemagglutinin as identified in UniProtKB Acc. No. P08362, last modified Aug. 1, 1988—v1; nucleoprotein from mumps virus, including nucleoprotein as identified in UniProtKB Acc. No. Q77IS8, last modified: Jul. 5, 2004—v1; glycoprotein E1 or E2 from rubella virus, including glycoprotein E1 or E2 as identified in UniprotKb Acc. No. P08563, last modified: May 30, 2006—v2; immediate early 62 (IE62) protein from varicella zoster virus, including IE62 protein as identified in UniprotKb Acc. No. P09310, last modified: Jul. 1, 1989—v1; E6 or E7 protein from HPV16 or HPV18, including E6 or E7 protein as identified in UniprotKb Acc. Nos. P03126 (last modified: Jul. 21, 1986—v1), P03129 (last modified: Jul. 21, 1986—v1), P06463 (last modified: Jan. 1, 1988—v1) or P06788 (last modified: Apr. 1, 1990—v2); Spr96/2021, PV7 (7-valent) and/or PV13 (13-valent), preferably derived from or based on *Streptococcus pneumoniae; Neisseria* heparin binding antigen (NHBA), factor H binding protein (fHbp) or Neisserial adhesin A (nadA) from *Neisseria meningitides*, including NHBA as identified in UniprotKb Acc. No. Q7WYZO (last modified: Oct. 1, 2003—v1), fHbp as identified in UniprotKb Acc. No. B2CQ00 (last modified May 20, 2008—v1) or nadA as identified in UniprotKb Acc. No. Q9K105 (last modified Oct. 1, 2000—v1); VP8 or VP6 from rotaviruses, including VP8 as identified in UniprotKb Acc. No. P12473 (last modified: Mar. 24, 2009—v2) or VP6 as identified in UniprotKb Acc. No. P04509 (last modified: May 30, 2000—v2); and diphtheria toxin from *Corynebacterium diphtheria*, including a detoxified variant thereof referred to as CRM-197. It is noted that when reference is made to polypeptides employed in a prior vaccination, also included in said terminology are detoxified and immunogenic variants or parts of said polypeptides. Thus, preferably, an antigenic polypeptide as described herein is a recall antigen, more preferably a microbial recall antigen.

Preferably, the antigenic polypeptide chosen is matched with existing immunity (preferably memory immunity in the form of memory T-cells and/or B-cells) in a subject, such that vaccination with such an antigenic polypeptide as immunogen, and tumor marking with such an antigenic polypeptide, taps into said pre-existing immunity (i.e. activates memory T-cells and/or B-cells to mount an immune response against said tumor). The skilled person can easily establish whether immunity against an antigenic polypeptide exists. Preferably, the pre-existing immunity was generated prior to establishment of a tumor, more preferably early in life for instance between the age of 0-20 years, even more preferably between the age of 1-12 or 1-6 years. In order to capitalize on pre-existing immunity, dormant immune cells are preferably reactivated by at least one immunization with an immunogenic composition as described herein.

It is therefore preferred that the antigenic polypeptide used in aspects of this invention is not previously encountered by a subject as part of an immune response against a tumor, more preferably it is (i) not (or rarely) encountered by a human subject as part of an immune response, or (ii) is encountered as part of an immune response, but not an immune response against a tumor, and wherein protective immunity is present in a subject.

Preferably the antigenic polypeptide as described herein mounts an immune response in cancer patients, preferably patients suffering from a tumor. Preferably, the antigenic polypeptide mounts an immune response in at least 90% of the patients intended for potential vaccination using methods of the present invention. The immune response thus mounted in cancer patients can be a de novo response due to the fact that the patients' immune system has not previously encountered this immunogen.

In the combination product for use according to the invention, the polypeptide is preferably a non-mammalian polypeptide, such as a microbial polypeptide, or a synthetic polypeptide. In addition, in a combination product for use according to the invention, the polypeptide is preferably selected from the group formed by keyhole limpet hemocyanin (KLH), green fluorescent protein (GFP) including enhanced green fluorescent protein (eGFP), luciferase, beta-galactosidase and a diphtheria toxin.

The term "microbial polypeptide", as used herein, refers to a polypeptide of a micro-organism, which includes bacteria, archaea, protists, fungi, unicellular plants and viruses.

Preferably, the non-human antigenic polypeptide is a bacterial polypeptide, a polypeptide originating from an organism of the Archaea domain, a fungal polypeptide or a viral polypeptide. Also preferred is a plant polypeptide. Also envisaged are a non-human mammalian polypeptide such as a polypeptide of a non-human primate, a rodent (e.g. mice and rats), a rabbit, a pig, a sheep, a goat, a cow, a horse and a donkey, a birds (e.g., a chicken, a turkey, a duck, a goose and the like). The antigenic polypeptide can also be a polypeptide of a snail or other mollusk, preferably one of the genus of *Megathura*, more preferably *Megathura crenulata.*

Most preferred are antigenic polypeptides that are not mammalian polypeptides, since non-mammalian antigenic polypeptides are more immunogenic than mammalian polypeptides when administered to a human subject. Examples of suitable non-mammalian antigenic polypeptides are for instance green fluorescent protein (GFP) including enhanced green fluorescent protein (eGFP), luciferase and beta-galactosidase.

One example of a highly preferred antigenic polypeptide is Keyhole Limpet Hemocyanin (KLH) of *Megathura crenulata*. KLH can be either KLH1 (amino acid sequence is provided in UniProtKB—Q53IP9, last modified: Feb. 19, 2014—v2) or KLH2 (amino acid sequence is provided in UniProtKB—Q1MVA1, last modified: May 30, 2006—v1). KLH is an example of a highly immunogenic antigen, which has been widely used as a universal immunogen and vaccine carrier.

Another example of a highly preferred antigenic polypeptide is a diphtheria toxin, which term includes detoxified variants thereof such as cross-reacting material (CRM)-197. Preferably, diphtheria toxin has the amino acid sequence as indicated in SEQ ID NO:1. A preferred detoxified variant of diphtheria toxin is CRM-197, which has the amino acid sequence as indicated in SEQ ID NO:1, except for glycine (G) at amino acid residue position 52 being substituted with glutamic acid (E). The term also includes variants of diphtheria toxin that have at least 90%, preferably at least 95%, 96%, 97%, 98% or at least 99% sequence identity to SEQ ID NO:1 or to a part of SEQ ID NO:1 having a continuous stretch of least 100, at least 200 or at least 300 amino acid residues, preferably wherein said continuous stretch is in—or is—the amino acid region indicated by positions 1-385 of SEQ ID NO:1. Alternatively, such variants include proteins having the amino acid sequence of SEQ ID NO:1, except that 1-50, preferably 1-20, more preferably 1-10, amino acid residues are deleted, inserted or substituted. Such variants preferably exhibit antigenicity and/or immunogenicity as described herein.

The term "% sequence identity" is defined herein as the percentage of amino acids in an amino acid sequence that is identical with the amino acids in an amino acid sequence of interest, after aligning the sequences and optionally introducing gaps, if necessary, to achieve the maximum percent sequence identity. Methods and computer programs for alignments are well known in the art. Sequence identity is calculated over substantially the whole length, preferably the whole (full) length, of an amino acid sequence of interest. The skilled person understands that consecutive amino acid residues in one amino acid sequence are compared to consecutive amino acid residues in another amino acid sequence.

Preferably, in medical uses and methods of the invention wherein diphtheria toxin is employed for intratumoral delivery of an antigenic polypeptide, the tumor is a tumor that expresses the HB-EGF receptor, preferably a tumor that expresses the HB-EGF receptor selected from the group formed by ovarian tumor; lung tumor; bladder tumor; gastric tumor; pancreatic tumor; breast tumor; liver tumor preferably hepatocellular carcinoma; brain tumor preferably glioblastoma; neuroblastoma; lymphoma including Hodgkin lymphoma or non-Hodgkin lymphoma, preferably histiocytic lymphoma or anaplastic large cell lymphoma; and leukemia preferably AML, CML or ALL. More preferably, the tumor that expresses the HB-EGF receptor is a malignant tumor selected from the group formed by ovarian cancer; lung cancer; bladder cancer; gastric cancer; pancreatic cancer; breast cancer; hepatocellular carcinoma; brain cancer, preferably glioblastoma; neuroblastoma; lymphoma including Hodgkin lymphoma or non-Hodgkin lymphoma, preferably histiocytic lymphoma or anaplastic large cell lymphoma; and leukemia, preferably AML, CML or ALL.

The invention also relates to a fusion protein or protein-protein conjugate comprising a first protein linked to a second protein, wherein said first protein comprises a diphtheria toxin or a (HB-EGF) receptor-binding domain of diphtheria toxin and said second protein comprises a non-human antigenic polypeptide as described herein. A highly preferred diphtheria toxin is CRM-197. Preferably, said second protein is not diphtheria toxin. Said first protein is either directly coupled to said first protein or via a linker peptide sequence, such as a glycine-serine (GS), preferably repetitive, linker peptide sequence. Said second protein can be linked at the N-terminal or C-terminal side of said first protein. The term "fusion protein", as used herein, refers to a proteinaceous molecule comprising at least two proteins, including parts thereof, that are covalently linked together. Generally, said two proteins are derived from different proteins.

Alternatively, chemical cross-linkers can be used to link different proteins to each other. Such chemical cross-linking can thus be used to couple diphtheria toxin or the HB-EGF receptor-binding domain of diphtheria toxin to a second protein as described herein. The person skilled in the art preferably employs techniques that have been well established, such as maleimide- or succinimidyl ester-directed cross-linking (Mattson, G., et al. 1993 "A practical approach to crosslinking", Molecular Biology Reports 17:167-183). Therefore, the first protein and the second protein can also be coupled via so-called cross-linking or conjugation, for example via one or more, such as at least 1, 2, 3, 4, 5, 6, 7, 8, 9, 10, 11, 12, 13, 14, 15, 16, 17, 18, 19 or at least 20 maleimides or succinimidyl esters. The term "protein-protein conjugate", as used herein, refers to a proteinaceous molecule that comprises at least two proteins, including parts thereof, that are linked together via a chemical cross-linker. Chemical cross-linking can be performed by maleimide- or succinimidyl ester-directed cross-linking.

Preferably, said receptor-binding domain of diphtheria toxin has an amino acid sequence as indicated in SEQ ID NO:2 or SEQ ID NO:3. The receptor-binding domain of diphtheria toxin as described herein also includes a variant that (i) has at least 90%, preferably at least 95%, 96%, 97%, 98% or at least 99% sequence identity to SEQ ID NO:2 or SEQ ID NO:3; and which variant binds (is capable of binding) to the HB-EGF receptor and/or is internalized in a tumor cell upon binding to the HB-EGF receptor, or (ii) has the same amino acid sequence as indicated in SEQ ID NO:2 or SEQ ID NO:3, except that 1-30, preferably 1-20, more preferably 1-10, amino acid residues are deleted, inserted or substituted; and wherein said variant binds (is capable of binding) to the HB-EGF receptor and/or is internalized in a tumor cell upon binding to the HB-EGF receptor.

Preferably, the second protein is a non-human antigenic polypeptide as described herein, more preferably selected from the group formed by (i) keyhole limpet hemocyanin (KLH), green fluorescent protein (GFP) including enhanced green fluorescent protein (eGFP), luciferase, beta-galactosidase and diphtheria toxin, (ii) a microbial polypeptide employed in a prior vaccination of a subject as described herein, preferably wherein said prior vaccination was against an infectious disease, more preferably wherein said prior vaccination was against hepatitis A and/or B; diphtheria; tetanus; pertussis; influenza; *Haemophilus influenzae* type b; polio; measles; mumps; rubella; varicella, human papillomavirus, *Streptococcus pneumoniae, Neisseria meningitides* or rotaviruses; and/or (iii) VP3 from hepatitis A virus; tetanus toxin from *Clostridium tetani*; pertussis toxin from *Bordetella pertussis*; protein D from *Haemophilus influenzae*; Vp1 capsid protein from poliovirus; hemagglutinin from measles virus; nucleoprotein from mumps virus; glycoprotein E1 or E2 from rubella virus; immediate early 62 (1E62) protein from varicella zoster virus; E6 or E7 protein from HPV16 or HPV18; Spr96/2021, PV7 (7-valent) and/or PV13 (13-valent), preferably derived from or based on *Streptococcus pneumoniae; Neisseria* heparin binding antigen (NHBA), factor H binding protein (fHbp) or Neisserial adhesin A (nadA) from *Neisseria meningitides*; and VP8 or VP6 from rotaviruses.

Preferably, a fusion protein or protein-protein conjugate as described herein is employed in the medical uses and methods of the invention, and is preferably for use as a medicament. Preferably, a fusion protein or protein-protein conjugate as described herein is employed as the non-human antigenic polypeptide prepared for intratumoral delivery. It can also be employed in an immunogenic composition as described herein. Thus, embodiments that refer to non-human antigenic polypeptides prepared for intratumoral delivery and to immunogenic compositions comprising a non-human antigenic polypeptide, stand also in relation to a fusion protein or protein-protein conjugate as described herein. Importantly, when reference is made to a immunogenic composition as described herein, the skilled person will appreciate that either the fusion protein or protein-protein conjugate as a whole can be used or only the second protein thereof.

The invention also provides a nucleic acid encoding the fusion protein of the invention.

The invention also provides a fusion protein, protein-protein conjugate or nucleic acid of the invention for use in a method of eliciting or directing an immune response against a tumor in a subject, or for use in a method of marking a tumor in a subject as a target for an immune response; preferably wherein said subject is vaccinated with an immunogenic composition comprising said fusion protein, protein-protein conjugate or said second protein as an immunogen, or comprising a nucleic acid encoding said immunogen, and optionally one or more pharmaceutically-acceptable carriers, adjuvants, excipients and/or diluents.

Fusion proteins or protein-protein conjugates as described herein are preferably for parenteral administration, more preferably for intra-peritoneal or intratumoral administration. Preferably, a fusion protein or protein-protein conjugate as described herein is for administration in the form of a pharmaceutical formulations adapted for parenteral administration, more preferably intratumoral injection, which may comprise a carrier such as for instance an aqueous or oily solution, dispersion, emulsion and/or suspension.

Amino acid sequences of proteins or polypeptides as described herein can be produced by methods and means generally available in the art. For instance, the person skilled in the art will understand how to generate a DNA sequence that encodes a fusion protein as described herein and how to manufacture and isolate a nucleic acid molecule with said DNA sequence using generally known recombinant DNA techniques. The sequence of the nucleic acid molecule is preferably codon-optimized for expression in a host cell. In this way codons are used that are favored for high level expression in a specific host cell. Nucleic acid molecules are preferably inserted in an expression vector using recombinant DNA techniques known by the person skilled in the art. Expression vectors direct the expression of a fusion protein as described herein in a host cell. These expression vectors are preferably replicable in a host cell, either as episomes or as part of the chromosomal DNA. Further, the expression vector preferably comprises (i) a strong promoter/enhancer, such as the CMV or SV40 promoter, (ii) an optimal translation initiation sequence, such as a ribosomal binding site and start codon, preferably a KOZAK consensus sequence and (iii) a transcription termination sequence, including a poly(A) signal when the protein is expressed in eukaryotic cells. Suitable expression vectors include plasmids and viral vectors such as adenoviruses, adeno-associated viruses and retroviruses. The person skilled in the art will understand that the expression vector to be used is dependent on the host cell that is used for expression of a recombinant protein. An expression vector is preferably suited for expression of a nucleic acid in a prokaryotic cell including a bacterial cell, or, more preferred, in a eukaryotic host cell, such as a yeast cell and a mammalian cell. A suitable example is mammalian expression vector pCMV4.

As an alternative, a nucleic acid molecule may be inserted in the genome of a host cell. Said insertion preferably is at a locus or within a region that ensures expression of a nucleic acid molecule of the invention in the host cell.

Suitable host cells include prokaryotic and eukaryotic cells, such as bacterial cells, yeast cells, insect cells, animal cells, mammalian cells, murine cells, rat cells, sheep cells, simian cells and human cells. Examples of suitable eukaryotic host cells include, but are not limited to HEK 293 cells, the hamster cell line CHO and BHK-21; the murine host cells NIH3T3, NSO and C127; the simian host cells COS and Vero; and the human host cells HeLa, PER.C6, U-937 and Hep G2. Suitable cells are available from public sources such as ATCC and Life Technologies. A number of transfection techniques are known in the art, see, e.g., Graham et al., 1973. Virology 52: 456; Green et al., 2012. "Molecular Cloning: A Laboratory Manual", CSHL Press; Davis et al., "Basic Methods in Molecular Biology", 1986, Elsevier; and Chu et al., 1981. Gene 13: 197. The person skilled in the art preferably employs techniques as described in these references to introduce one or more exogenous nucleic acid molecules into suitable host cells. An example of a host cell for the production of a fusion protein as described herein is a HEK 293 cell.

The antigenic polypeptide as described herein can also be a synthetic polypeptide, preferably a polypeptide that is designed for eliciting a strong cellular immune response upon administration to a human subject.

When the antigenic polypeptide is for administration as an immunogen, it may comprise a further polypeptide or conjugation partner so as to enhance elicitation of an immune response. Thus, said immunogen can be a fusion polypeptide comprising said antigenic polypeptide and for instance a carrier protein.

The combination product for according to the invention may be in fixed combination, a non-fixed combination or kit-of parts.

A "fixed combination" in the present invention is used as is known to a person skilled in the art and is defined as a combination wherein both components of the combination product are present together in one unit dosage or in a single entity. One example of a "fixed combination" is a pharmaceutical composition wherein both components of the combination product are present in admixture for simultaneous administration, such as in a formulation. Another example of a "fixed combination" is a pharmaceutical composition wherein both components of the combination product are present in one unit without being in admixture.

A non-fixed combination or "kit-of-parts" as used herein is known to a person skilled in the art and is defined as a combination product wherein both components are present in more than one unit. One example of a non-fixed combination or kit-of-parts is a combination product wherein both components of the combination product are present separately. The components of the non-fixed combination or kit-of-parts may be administered separately, sequentially, simultaneously, concurrently and/or chronologically staggered.

Preferably, the combination product for use of the invention, is a non-fixed combination product or kit of parts. Preferably, the components of the combination product are administered separately, sequentially and chronologically staggered.

Therefore, the product for use according to the invention is for separate, sequential, simultaneous, concurrent or chronologically staggered administration.

Preferably, in the combination product for use according to the invention, the polypeptide prepared for intratumoral delivery, or said nucleic acid encoding said polypeptide, and the immunogenic composition are for sequential administration; and wherein the polypeptide prepared for intratumoral delivery, or said nucleic acid encoding said polypeptide, is for administration following the administration of the immunogenic composition, or vice versa.

The invention also provides a non-human antigenic polypeptide, or a nucleic acid encoding said polypeptide, for use in eliciting or directing an immune response against a tumor in a subject; wherein said polypeptide or said nucleic acid is prepared for intratumoral delivery; and wherein said subject is vaccinated with an immunogenic composition comprising said polypeptide as an immunogen, or comprising a nucleic acid encoding said immunogen, and optionally one or more pharmaceutically-acceptable carriers, adjuvants, excipients and/or diluents. Preferably, the (i) polypeptide/nucleic acid prepared for intratumoral delivery, (ii) the immunogenic composition, and (iii) the medical use are as defined for a combination product of the invention. It is evident that tumor antigen-independent vaccination and tumor marking may, and preferably, occur separate in time, and that marking of a tumor as a target for an immune response elicited, may occur after the vaccination step. Therefore, preferably, said subject is vaccinated with (or is administered) the immunogenic composition as described herein prior to administration of said non-human antigenic polypeptide as described herein. Preferably, in the non-human antigenic polypeptide, or nucleic acid, for use as described herein, said polypeptide or said nucleic acid prepared for intratumoral delivery marks the tumor as a target for an immune response following intratumoral delivery. Preferably, in the non-human antigenic polypeptide, or nucleic acid, for use as described herein, following intratumoral delivery of said non-human antigenic polypeptide or nucleic acid encoding said polypeptide, an immune response specifically directed against said tumor is elicited.

The invention also provides a non-human antigenic polypeptide, or a nucleic acid encoding said polypeptide, for use in marking a tumor as a target for an immune response in a subject; wherein said polypeptide or said nucleic acid is prepared for intratumoral delivery as described herein. The invention also provides a method for marking a tumor as a target for an immune response in a subject, comprising the step of:—administering to a subject suffering from a tumor a pharmaceutically effective amount of a non-human antigenic polypeptide, or a nucleic acid encoding said polypeptide, prepared for intratumoral delivery as described herein. Preferably, said non-human polypeptide or said nucleic acid prepared for intratumoral delivery is for intratumoral administration, and is a dendritic cell, preferably a dendritic cell obtained from a cell of cell line DCOne as described herein, comprising said polypeptide or said nucleic acid encoding said polypeptide. In the same manner, the invention provides a dendritic cell, preferably a dendritic cell obtained from a cell of cell line DCOne as described herein, comprising a non-human polypeptide as described herein, or a nucleic acid encoding said polypeptide, for use in marking a tumor as a target for an immune response in a subject, wherein said dendritic cell is for intratumoral administration. The invention also provides a dendritic cell, preferably a dendritic cell obtained from a cell of cell line DCOne as described herein, comprising a non-human polypeptide as described herein, or a nucleic acid encoding said polypeptide, for use as a medicament, preferably for use in tumor vaccination, tumor marking or the treatment of a tumor, wherein said dendritic cell is for intratumoral administration.

The invention also provides an immunogenic composition comprising a non-human antigenic polypeptide as an immunogen, or comprising a nucleic acid encoding said immunogen, for use in eliciting an immune response against a tumor in a subject; wherein said subject has a tumor marked as a target for an immune response following administration of said non-human antigenic polypeptide, or a nucleic acid encoding said polypeptide, prepared for intratumoral delivery as described herein. Preferably, the (i) polypeptide/nucleic acid prepared for intratumoral delivery, (ii) the immunogenic composition, and (iii) the medical use are as defined for a combination product of the invention.

The invention also provides a combination product for use according to the invention, for use in the treatment of a tumor.

The invention also provides a use of a non-human antigenic polypeptide prepared for intratumoral delivery as described herein and/or an immunogenic composition as described herein for the manufacture of a combination product for eliciting an immune response against a tumor in a subject, preferably for treating a subject suffering from a tumor. Preferably, the (i) polypeptide/nucleic acid prepared for intratumoral delivery, (ii) the immunogenic composition, and (iii) the medical use are as defined for a combination product of the invention.

The invention also provides a method for eliciting an immune response against a subject suffering from a tumor, comprising the steps of administering to a subject suffering from a tumor a pharmaceutically effective amount of a non-human antigenic polypeptide, or a nucleic acid encoding said polypeptide, prepared for intratumoral delivery; and administering to said subject a pharmaceutically effective amount of an immunogenic composition comprising said polypeptide as an immunogen, or comprising a nucleic acid encoding said immunogen, and optionally one or more pharmaceutically-acceptable carriers, adjuvants, excipients and/or diluents. Preferably, the (i) polypeptide/nucleic acid prepared for intratumoral delivery, (ii) the immunogenic composition, and (iii) the medical use are as defined for the combination product of the invention.

Preferably, such a method further comprises the step of allowing an MHC peptide antigen complex to be produced from said polypeptide following intratumoral delivery of said polypeptide, or said nucleic acid encoding said polypeptide, prepared for intratumoral delivery.

Preferably, in such a method of the invention, said immunogenic composition elicits a T cell mediated immune response against said intratumoral polypeptide, preferably a T-cell mediated immune response against said MHC peptide antigen complex.

The invention also provides a method of eliciting or directing an immune response against a tumor in a subject, comprising the step of:—administering to a subject suffering from a tumor a pharmaceutically effective amount of a non-human antigenic polypeptide, or a nucleic acid encoding said polypeptide, prepared for intratumoral delivery; wherein said subject is vaccinated with an immunogenic composition comprising said polypeptide as an immunogen, or comprising a nucleic acid encoding said immunogen, and optionally one or more pharmaceutically-acceptable carriers, adjuvants, excipients and/or diluents. In this aspect, the subject has already been vaccinated with an immunogenic composition as described herein, and subsequent marking of the tumor allows for directing the elicited immune response to said tumor. Preferably, the (i) polypeptide/nucleic acid prepared for intratumoral delivery, (ii) the immunogenic composition, and (iii) the medical use are as defined for the combination product of the invention.

The invention also provides a method of eliciting an immune response against a tumor in a subject, comprising the step of:—administering to a subject suffering from a tumor a pharmaceutically effective amount of an immunogenic composition comprising a non-human antigenic polypeptide as an immunogen, or comprising a nucleic acid encoding said immunogen, and optionally one or more pharmaceutically-acceptable carriers, adjuvants, excipients and/or diluents; wherein said subject is administered said non-human antigenic polypeptide, or a nucleic acid encoding said polypeptide, prepared for intratumoral delivery. In this aspect, the subject has a tumor that has been marked as a target for an immune response as described herein. Subsequent vaccination allows for elicitation of an immune response directed to said already marked tumor. Preferably, the (i) polypeptide/nucleic acid prepared for intratumoral delivery, (ii) the immunogenic composition, and (iii) the medical use are as defined for the combination product of the invention.

The invention also provides a method for treating a subject suffering from a tumor, comprising the step of administering to a subject suffering from a tumor a pharmaceutically effective amount of a combination product as described herein, wherein the combination product is for separate, sequential, simultaneous, concurrent or chronologically staggered administration.

In the medical uses described herein, administration of the respective components is in a pharmaceutically effective amount or dose.

The term "pharmaceutically effective amount", as used herein, refers to an amount effective, at dosages and for periods of time necessary, to achieve the desired effects. For instance, the desired effect of an antigenic polypeptide as described herein that is prepared for intratumoral delivery, is marking a tumor as a target for an immune response. For instance, the desired effect of an immunogenic composition as described herein is to elicit an immune response against a tumor in a subject that is marked as target for said immune response.

For the purpose of clarity and a concise description, features are described herein as part of the same or separate aspects and preferred embodiments thereof, however, it will be appreciated that the scope of the invention may include embodiments having combinations of all or some of the features described. For instance, embodiments relating to polypeptides may also apply to nucleic acids encoding such polypeptides, and vice versa. The same applies for instance to embodiments that relate to medical uses defined in product for use, use and method format. Further, it is to be understood that, when the description provides details in the form of embodiments of features that are also mentioned in the claims, inter alia such embodiments are disclosed in relation to the claims.

The content of the documents referred to herein is incorporated by reference.

FIGURE LEGENDS

Figure 1B:
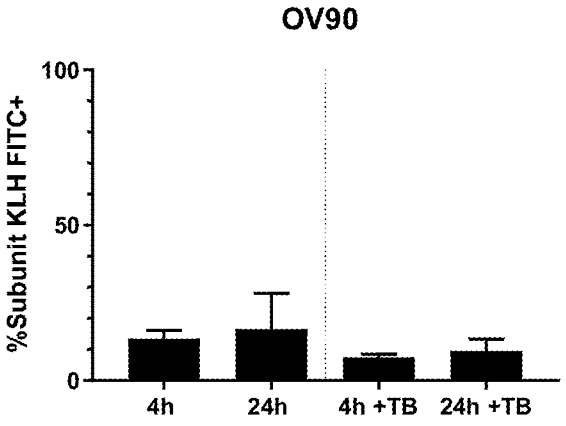

FIGS. 1A-1B. Uptake of subunit KLH protein by DCOne mDC (n=3) (FIG. 1A) and labelling of OV90 ovarian cancer cells (n=2) (FIG. 1B) after 4 hours and 24 hours. 0.08% trypan blue (TB) was added to quench extracellular bound subunit KLH-FITC to visualize the percentage intracellular subunit KLH-FITC.

Figure 2A:
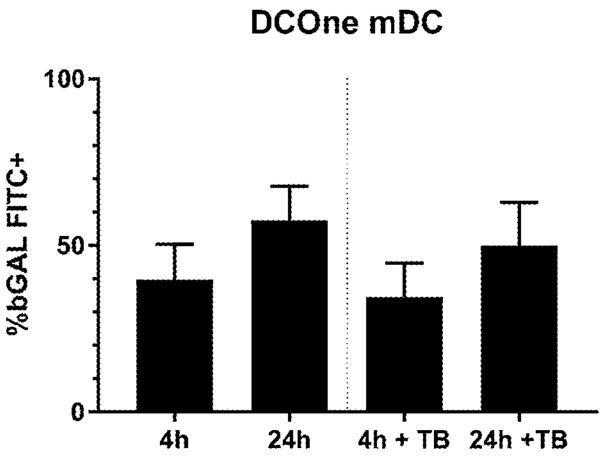
Figure 2B:
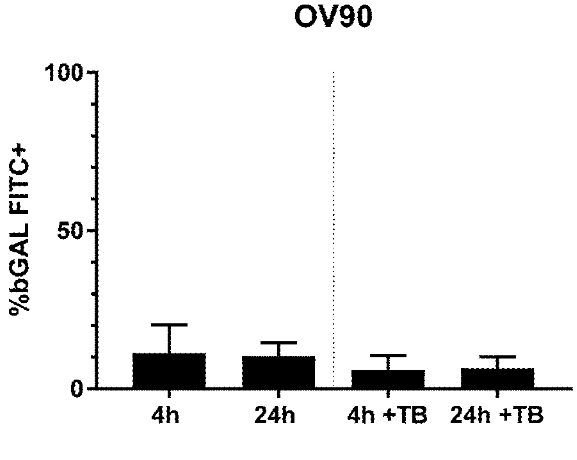

FIGS. 2A-2B. Uptake of ß-galactosidase protein by DCOne mDC (n=3) (FIG. 2A) and labelling of OV90 ovarian cancer cells (n=2) (FIG. 2B) after 4 hours and 24 hours. 0.08% trypan blue was added to quench extracellular bound ß-galactosidase-FITC to visualize the percentage intracellular ß-galactosidase-FITC.

Figure 3A:
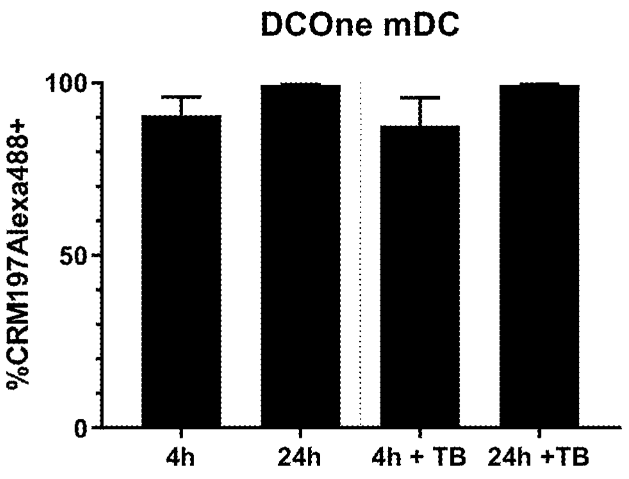
Figure 3B:
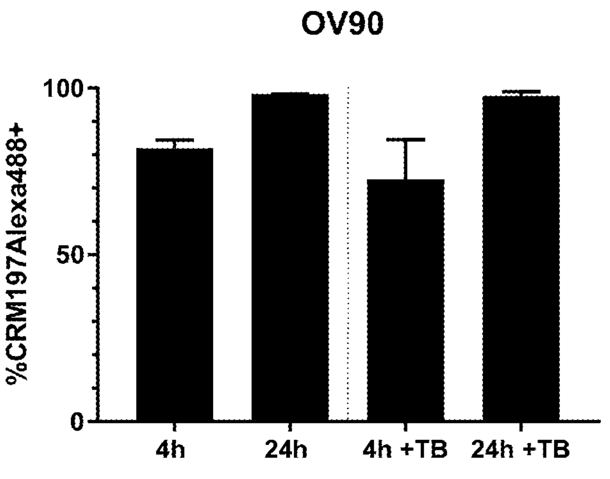

FIGS. 3A-3B. Uptake of CRM197 protein by DCOne mDC (n=2) (FIG. 3A) and labelling of OV90 ovarian cancer cells (n=2) (FIG. 3B) after 4 hours and 24 hours. 0.08% trypan blue was added to quench extracellular bound CRM197-Alexa488 to visualize the percentage intracellular CRM197-Alexa488.

FIG. 4. Tumor growth inhibition in a humanized U87-MG glioblastoma model.

FIG. 5. Tumor growth inhibition in a humanized A375 melanoma model.

Figure 6A:
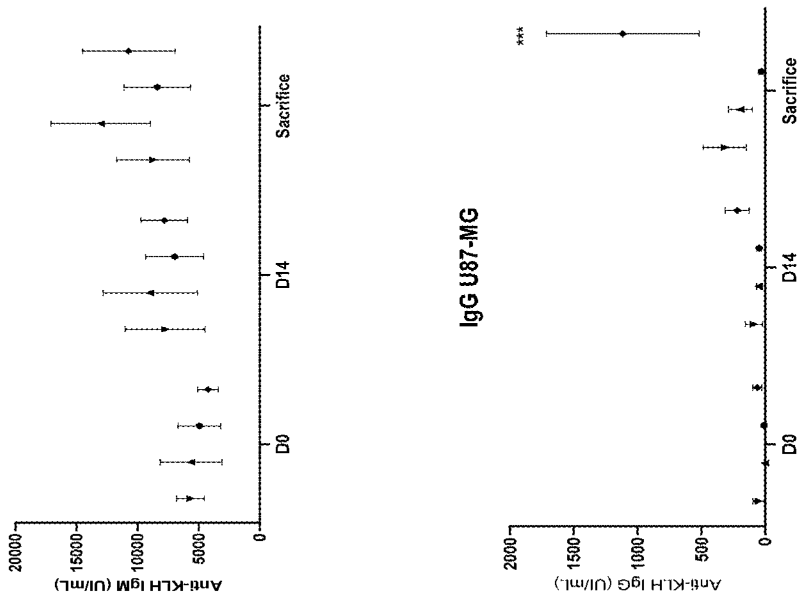
Figure 6B:
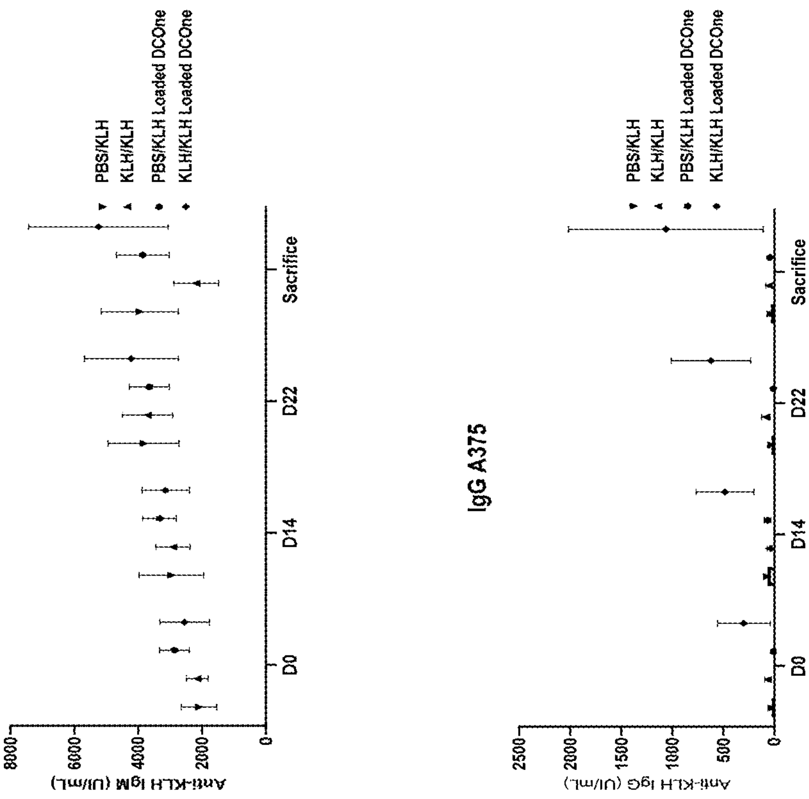

FIGS. 6A-6B. anti-KLH IgG and IgM level in the serum of mice over time. Anti-KLH IgM and anti-KLH IgM concentration (UI/mL) measured with an Elisa test on the serum of mice taken at D0, D14 and at sacrifice. N=5 mice per group. Graphs represent the individual data of anti-KLH IgG and IgM per group ((FIG. 6A) is glioblastoma group, (FIG. 6B) is melanoma group). Two way ANOVA with Dunnet's multiple comparison test was used. *vs vehicle group, *<0.05, <0.01, *<0.001, ****<0.0001).

SEQUENCE LISTING

```
SEQUENCE LISTING
SEQ ID NO: 1: Diphtheria toxin
   1  GADDVVDSSK SFVMENFSSY HGTKPGYVDS IQKGIQKPKS
      GTQGNYDDDW KGFYSTDNKY

  61  DAAGYSVDNE NPLSGKAGGV VKVTYPGLTK VLALKVDNAE
      TIKKELGLSL TEPLMEQVGT

 121  EEFIKRFGDG ASRVVLSLPF AEGSSSVEYI NNWEQAKALS
      VELEINFETR GKRGQDAMYE

 181  YMAQACAGNR VRRSVGSSLS CINLDWDVIR DKTKTKIESL
      KEHGPIKNKM SESPNKTVSE
```

-continued

```
241  EKAKQYLEEF HQTALEHPEL SELKTVTGTN PVFAGANYAA
     WAVNVAQVID SETADNLEKT

301  TAALSILPGI GSVMGIADGA VHHNTEEIVA QSIALSSLMV
     AQAIPLVGEL VDIGFAAYNF

361  VESIINLFQV VHNSYNRPAY SPGHKTQPFL HDGYAVSWNT
     VEDSIIRTGF QGESGHDIKI

421  TAENTPLPIA GVLLPTIPGK LDVNKSKTHI SVNGRKIRMR
     CRAIDGDVTF CRPKSPVYVG

481  NGVHANLHVA FHRSSSEKIH SNEISSDSIG VLGYQKTVDH
     TKVNSKLSLF FEIKS

SEQ ID NO: 2: Receptor-binding domain of
diphtheria toxin (a.a. 385-535 of SEQ ID NO: 1)
385      KTQPFL HDGYAVSWNT VEDSIIRTGF QGESGHDIKI
     TAENTPLPIA GVLLPTIPGK

441  LDVNKSKTHI SVNGRKIRMR CRAIDGDVTF CRPKSPVYVG
     NGVHANLHVA FHRSSSEKIH

501  SNEISSDSIG VLGYQKTVDH TKVNSKLSLF FEIKS

SEQ ID NO: 3: Receptor-binding domain of
diphtheria toxin (a.a. 387-535 of SEQ ID NO: 1)
387        QPFL HDGYAVSWNT VEDSIIRTGF QGESGHDIKI
     TAENTPLPIA GVLLPTIPGK

441  LDVNKSKTHI SVNGRKIRMR CRAIDGDVTF CRPKSPVYVG
     NGVHANLHVA FHRSSSEKIH

501  SNEISSDSIG VLGYQKTVDH TKVNSKLSLF FEIKS
```

EXAMPLES

Materials and Methods

Generation of DCOne Mature Dendritic Cells (mDC)

DCOne progenitors (as deposited with the DSMZ under accession number DSMZ ACC3189 on 15 Nov. 2012) were differentiated and matured according to the procedure described in WO2009019320 A2. Cells were counted and phenotypic analysis of DCOne mDC cells was performed using flow cytometry (FACSVerse; BDBiosciences).

Culture of Ovarian Cancer Cells

OV90 ovarian cancer cell were cultured in medium199/MCDB105 medium (1:1) containing 15% FBS and 2% P/S) in an incubator at 37° C. with 5% $CO_2$. OV90 cells were obtained from ATCC.

Uptake of Foreign Antigens by DCOne mDC

Uptake by DCOne mDC was assessed for three different foreign antigens at a final concentration of 10 μg/mL for 4 hours and 24 hours during maturation. 750.000 cells were seeded into 6 well plates for each condition. The antigens used were CRM197-Alexa488, subunit KLH-FITC and β-galactosidase-FITC. CRM197-Alexa488 was purchased from Fina Biosolutions. Subunit KLH was purchased from Stellar Biotechnologies Inc. β-galactosidase was purchased from Roche. Subunit KLH and β-galactosidase were conjugated in-house to fluorochrome fluorescein isothiocyanate (FITC) using a FITC labelling kit according to manufacturer's protocol. Uptake of foreign antigens was assessed by flow cytometry. 0.08% Trypan blue was used to quench externally bound protein, to visualize only the internalized protein.

Labelling of Tumor Cells with Foreign Antigens

The labelling of OV90 ovarian cancer cells was assessed for three different foreign proteins at a final concentration of 10 μg/mL for 4 hours and 24 hours. 100.000 cells were seeded into 96 well plates for each condition. The proteins used were CRM197-Alexa488, Subunit KLH-FITC and β-galactosidase-FITC. Labelling of tumor cells in vitro was assessed by flow cytometry as mentioned above for DCOne mDCs.

Humanized U87-MG Glioblastoma Mouse Model

Four-week-old immunodeficient female NOD/Shi-scid/IL-2Rynull immunodeficient mouse strain (NCG; Taconic) were engrafted with intravenous (IV) injection of 5e4 cord blood-derived $CD34^+$ hematopoietic stem and progenitor cells (French Blood Bank) two days after chemical myeloablative treatment. Humanized mice were enhanced for dendritic cell populations with a GM-CSF/IL3/IL4 hydrodynamic boost and Flt3L recombinant protein. After 7 days mice were inoculated subcutaneously in the right flank with $1e^6$ U87-MG glioblastoma cells/mouse (Sigma Aldrich) for tumor engraftment. Approximately 15 days after tumor engraftment mice were randomised and divided into different vaccination groups including 5 mice per group. All mice received 1 intraperitoneal (i.p.) vaccination and one intratumoral (i.t.) injection marking the tumor.

Mice received 100 μg KLH per i.p. injection or a 100 μl PBS i.p. injection, and were injected with 200.000 KLH-loaded DCOne mDCs i.t. or 100 μg KLH in 50 μl i.t. according to following schedule:

Group 1 (PBS/KLH) received one i.p. PBS vaccination (on day 1 after randomization), and one i.t. injection with KLH (on day 8 after randomization).

Group 2 (KLH/KLH) received one i.p. KLH vaccination (on day 1 after randomization), and one i.t. injection with KLH (on day 8 after randomization).

Group 3 (PBS/KLH loaded DCOne) received one i.p. PBS vaccination (on day 1 after randomization), and one i.t. injection with KLH loaded DCOne mDC (on day 8 after randomization).

Group 4 (KLH/KLH loaded DCOne) received one i.p. KLH vaccination (on day 1 after randomization), and one i.t. injection with KLH loaded DCOne mDC (on day 8 after randomization).

Subunit KLH was purchased from Stellar Biotechnologies Inc. Tumor growth reduction and induction of immune responses were measured.

Humanized A375 Melanoma Mouse Model

After humanization with $CD34^+$ stem cells and hydrodynamic boost with cytokines as described above, mice were inoculated subcutaneously in the right flank with $2e^6$ A375 melanoma cells/mouse (Sigma Aldrich) for tumor engraftment. Approximately 15 days after tumor engraftment mice were randomized and divided into different vaccination groups including 5 mice per group. The mice received two intraperitoneal (i.p.) vaccinations and thereafter one intratumoral (i.t.) injection for marking the tumor.

Mice received 100 μg KLH in 100 μl per i.p. injection or a 100 μl PBS i.p. injection, and were injected with 200.000 KLH-loaded DCOne mDCs or 100 μg KLH in 50 μl i.t. according to the following schedule:

Group 1 (PBS/KLH) received two i.p. PBS vaccinations (on days 1 and 8 after randomization), and one i.t. injection with KLH (on day 15 after randomization).

Group 2 (KLH/KLH) received two i.p. KLH vaccinations (on days 1 and 8 after randomization), and one i.t. injection with KLH (on day 15 after randomization).

Group 3 (PBS/KLH loaded DCOne) received two i.p. PBS vaccinations (on days 1 and 8 after randomization), and one i.t. injection with KLH loaded DCOne mDC (on day 15 after randomization).

Group 4 (KLH/KLH loaded DCOne) received two i.p. KLH vaccinations (on days 1 and 8 after randomization), and one i.t. injection with KLH loaded DCOne mDC (on day 15 after randomization).

Subunit KLH was purchased from Stellar Biotechnologies Inc. Tumor growth reduction and vaccination induced immune responses were measured.

Example 1. Uptake of Foreign Proteins

Uptake of Subunit KLH-FITC by DCOne mDC

DCOne mDC were loaded with fluorochrome-conjugated subunit KLH during maturation process for 4 hours and 24 hours as described in the material and methods section. The internalization of subunit KLH was analysed using flow cytometer. Trypan blue quenches the cell surface-bound antigen and was used to distinguish between surface-bound antigen and internalized antigen. The observed internalization of subunit KLH-FITC by DCOne mDC after 4 hrs was 54.6±8.8%, and 49.9±9.8% with trypan blue and after 24 hours 86.1±7.0%, and 81.7±8.0% with trypan blue indicating effective antigen uptake by DCOne mDC (FIG. 1A).

Labelling of OV90 Tumor Cells with Subunit KLH

OV90 ovarian carcinoma cells were cultured with subunit KLH-FITC for 4 hours and 24 hours as described in the material and methods section. We observed 13.5±2.6%, labelling of OV90 for 4 hours of which 7.5±1.0% of cells with intracellular antigen as demonstrated by quenching of surface-bound subunit KLH-FITC signal with trypan blue, and after 24 hours 16.5±11.5% of OV90 cells were labelled with antigen with 9.5±3.8% of antigen inside the cells (FIG. 1B).

Uptake of β-Galactosidase-FITC by DCOne mDC

DCOne mDCs were incubated with β-galactosidase-FITC for 4 hrs and 24 hrs as described in the materials and methods section. The uptake of β-galactosidase-FITC was measured using flow cytometry in the absence or presence of trypan blue in order to distinguish between extracellularly bound and internalized β-galactosidase-FITC. FIG. 2A depicts that after 4 hrs incubation 39.7±10.7% of DCOne mDC have internalized β-galactosidase-FITC as the trypan blue quenching hardly affected the signal (34.5±10.2%) indicating intracellular localization of β-galactosidase-FITC in DCOne mDC. The internalisation of β-galactosidase-FITC by DCOne mDC was increased after 24 hours i.e. 57.6±10.2%, and 49.9±13.0% with trypan blue indicating intracellular β-galactosidase-FITC.

Labelling of OV90 by β-Galactosidase-FITC

The labelling of ovarian cancer cell line OV-90 with β-galactosidase-FITC after 4 hours and 24 hours was 11.3±8.9% (6.0±4.6% with trypan blue) and 10.4±4.2%, (6.5±3.6% with trypan blue) respectively showing both surface-bound and intracellular presence of β-galactosidase-FITC (FIG. 2B).

Uptake of CRM197 by DCOne mDC

During maturation process DCOne mDC were cultured with CRM197-Alexa488 for 4 and 24 hours as described in the materials and methods section. After 4 and 24 hours uptake of antigen CRM-197 by DCOne mDCs was analysed using a flow cytometer in the presence and absence of trypan blue as mentioned in above sections. We observed that 90.6±5.4% and 99.4±0.1 of DCOne mDC had efficiently internalized CRM-197 after 4 and 24 hours respectively and that trypan blue quenching did not affect the results (87.6±8.0% and 99.5±0.2% respectively; FIG. 3A).

Labelling of OV90 Tumor Cells with CRM197

The percentage of CRM197-Alexa488 uptake after 4 hours by OV90 tumor cells was 82.0±2.5%, and after 24 hours labelling increased up to 98.2±0.1% (FIG. 3B). The trypan blue quenching did not affect the signal indicating that CRM-197 is predominantly present inside the cell (72.7±11.9% and 97.6±1.4% with trypan blue after 4 and 24 hours respectively).

The in vitro data of uptake of foreign proteins by DCOne mDCs showed that DCOne mDCs are very efficient in internalizing foreign protein. All foreign proteins tested, CRM197, KLH and β-galactosidase are taken up very well by DCOne mDCs. DCOne cells can thus be used as a carrier for vaccination and/or intratumoral delivery of foreign proteins.

The data of uptake of foreign proteins by ovarian cancer cells showed that ovarian cancer cells are more specific in internalizing foreign protein as compared to DCOne cells. CRM197 is taken up very efficiently by receptor-mediated endocytosis (Moya et al. *J Cell Biol,* 101(2):548-59 (1985)) in tumor cells due to presence of the specific HB-EGF receptor for diptheria toxin/CRM197 as described in literature (e.g. Miyamoto et al. *Cancer Sci,* 97(5):341-7 (2006)), while uptake of KLH and β-galactosidase is lower. These findings show that a tumor can be marked by foreign proteins. This is especially the case for CRM197, which can therefore potentially be used as a carrier for tumor marking with other foreign protein coupled to CRM197.

Example 2. Tumor Growth Inhibition in a Humanized U87-MG Glioblastoma Mouse Model and in a Humanized A375 Melanoma Mouse Model The U87-MG mice received one i.p. vaccination of either PBS or KLH and one i.t. injection to mark the tumor either with KLH or KLH-loaded DCOne mDCs. Tumor growth was monitored three times per week using a digital caliper. Tumor volumes (in mm3) were calculated according to the following formula: Volume=(width×length^2)/2. At day 18, we observed a slowed tumor growth in vaccinated mice as compared to the mice injected with PBS, with i.t. injection of KLH-loaded DCOne having the strongest effect (FIG. 4).

The A375 melanoma mice received two i.p. vaccinations of either PBS or KLH and one i.t. injection to mark the tumor either with KLH or KLH-loaded DCOne mDCs. Tumor growth was monitored three times per week using a digital caliper. Tumor volumes (in mm3) were calculated according to the following formula: Volume=(width×length^2)/2. As with the U87-MG mice, we observed that the vaccinated group of mice had a slowed tumor growth compared to the groups injected with PBS (FIG. 5). This effect was strongest in the mice treated with KLH/KLH loaded DCOne.

These in vivo data in humanized mice show that vaccination followed by intratumoral injection (tumor marking) leads to slowed tumor growth in two separate solid tumor models, particularly when tumor marking was carried out using DCOne mDCs as a carrier. Although not statistically significant, the trend of slowed tumor growth was consistent in two separate solid tumor models.

Example 3. T Cell Mediated KLH-Specific Antibody Production

Possible antibody responses against KLH resulting from intratumoral injection and/or vaccination was quantified by ELISA (D0, D14 and sacrifice). We observed that both in U87-MG and A375 mice, there was no significant difference regarding anti-KLH IgM concentration between treated groups and the PBS control group over time. However, we surprisingly observed that mice from the KLH/KLH loaded DCOne group produced significantly more anti-KLH IgG than the PBS control group at sacrifice (FIGS. 6A-6B). This implies a T cell dependent IgM to IgG switch (Geha et al., *NEJM,* 330:1008-1009 (1994)).

The invention claimed is:

1. A method for generating an immune response against a solid tumor in a subject comprising:

a vaccination step comprising administering a first composition to the subject at a site distal to a solid tumor site, wherein the first composition comprises a CD34-positive, CD1a-positive, and CD83-positive cell and a non-tumor antigen or a nucleic acid encoding the non-tumor antigen; and a tumor-marking step comprising administering a second composition to the subject at the solid tumor site, wherein the second composition comprises the non-tumor antigen or a nucleic acid encoding the non-tumor antigen, wherein the time between the vaccination step and the tumor-marking step is within 21 days thereby generating an immune response against the solid tumor in the subject.

2. The method of claim 1, further comprising one or more booster steps each comprising administering a booster composition to the subject, wherein the booster composition comprises the non-tumor antigen or a nucleic acid encoding the non-tumor antigen.

3. The method of claim 1, wherein the tumor marking-step comprises administering the second composition into the tumor.

4. The method of claim 1, wherein the vaccination step comprises administering the first composition via a route selected from the group consisting of intramuscular, intradermal, subcutaneous, intravenous, intraarterial, intraperitoneal, delivery to the interstitial space of a tissue, and delivery to a non-tumor tissue.

5. The method of claim 1, wherein the tumor-marking step is performed subsequent to the vaccination step.

6. The method of claim 1, wherein the solid tumor is selected from the group consisting of glioblastoma and ovarian cancer.

7. The method of claim 1, wherein the second composition is further comprises a tumor targeting component selected from the group consisting of a tumor-specific virus, an oncolytic virus, and a tumor-specific nanoparticle.

8. The method of claim 1, wherein the CD34-positive, CD1a-positive, and CD83-positive cell is differentiated from DCOne.

9. The method of claim 1, wherein the first and second compositions each comprise one or more pharmaceutically-acceptable carriers, adjuvants, excipients and/or diluents.

10. A method for generating an immune response against a solid tumor in a subject comprising:

a vaccination step comprising administering a first composition to the subject at a site distal to a solid tumor site, wherein the first composition comprises a non-tumor antigen or a nucleic acid encoding the non-tumor antigen; and a tumor-marking step comprising administering a second composition to the subject at the solid tumor site, wherein the second composition comprises a CD34-positive, CD1a-positive, and CD83-positive cell and the non-tumor antigen or a nucleic acid encoding the non-tumor antigen, wherein the time between the vaccination step and the tumor-marking step is within 21 days, thereby generating an immune response against the solid tumor in the subject.

11. The method of claim 10, further comprising one or more booster steps each comprising administering a booster composition to the subject, wherein the booster composition comprises the non-tumor antigen or a nucleic acid encoding the non-tumor antigen.

12. The method of claim 10, wherein the tumor marking-step comprises administering the second composition into the tumor.

13. The method of claim 10, wherein the vaccination step comprises administering the first composition via a route selected from the group consisting of intramuscular, intradermal, subcutaneous, intravenous, intraarterial, intraperitoneal, delivery to the interstitial space of a tissue, and delivery to a non-tumor tissue.

14. The method of claim 10, wherein the tumor-marking step is performed subsequent to the vaccination step.

15. The method of claim 10, wherein the solid tumor is selected from the group consisting of glioblastoma and ovarian cancer.

16. The method of claim 10, wherein the second composition further comprises a tumor targeting component selected from the group consisting of a tumor-specific virus, an oncolytic virus, and a tumor-specific nanoparticle.

17. The method of claim 10, wherein the CD34-positive, CD1a-positive, and CD83-positive cell is differentiated from DCOne.

18. The method of claim 10, wherein the first and second compositions each comprise one or more pharmaceutically-acceptable carriers, adjuvants, excipients and/or diluents.

19. A method for generating an immune response against a solid tumor in a subject comprising:

a vaccination step comprising administering a first composition to the subject at a site distal to a solid tumor site, wherein the first composition comprises a CD34-positive, CD1a-positive, and CD83-positive cell and a non-tumor antigen or a nucleic acid encoding the non-tumor antigen; and a tumor-marking step comprising administering a second composition to the subject at the solid tumor site, wherein the second composition comprises a CD34-positive, CD1a-positive, and CD83-positive cell and the non-tumor antigen or a nucleic acid encoding the non-tumor antigen, wherein the time between the vaccination step and the tumor-marking step is within 21 days, thereby generating an immune response against the solid tumor in the subject.

20. The method of claim 19, wherein the CD34-positive, CD1a-positive, and CD83-positive cell is differentiated from DCOne.

* * * * *